(12) United States Patent
Nelson et al.

(10) Patent No.: US 8,536,336 B2
(45) Date of Patent: Sep. 17, 2013

(54) PRODRUG COMPOUNDS USEFUL AS CANNABINOID LIGANDS

(75) Inventors: Derek W. Nelson, Highland Park, IL (US); Michael J. Dart, Highland Park, IL (US); Xueqing Wang, Northbrook, IL (US); Bo Liu, Waukegan, IL (US); Teodozyj Kolasa, Lake Villa, IL (US); Meena Patel, Green Oaks, IL (US)

(73) Assignee: AbbVie Inc., North Chicago, IL (US)

( * ) Notice: Subject to any disclaimer, the term of this patent is extended or adjusted under 35 U.S.C. 154(b) by 238 days.

(21) Appl. No.: 12/968,604

(22) Filed: Dec. 15, 2010

(65) Prior Publication Data

US 2011/0144165 A1 Jun. 16, 2011

Related U.S. Application Data

(60) Provisional application No. 61/286,845, filed on Dec. 16, 2009.

(51) Int. Cl.
C07D 513/04 (2006.01)
A61K 31/4365 (2006.01)

(52) U.S. Cl.
USPC .......................... 546/114; 514/301

(58) Field of Classification Search
USPC ........................ 546/114; 514/301
See application file for complete search history.

(56) References Cited

U.S. PATENT DOCUMENTS

| | | | |
|---|---|---|---|
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2008/0312435 A1 * | 12/2008 | Saito et al. | 544/133 |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0216760 A1 | 8/2010 | Frost | |

FOREIGN PATENT DOCUMENTS

| | | |
|---|---|---|
| EP | 1820504 A1 | 8/2007 |
| WO | WO9507271 A1 | 3/1995 |
| WO | WO9710223 A1 | 3/1997 |
| WO | WO2005099353 A2 | 10/2005 |
| WO | WO2006008754 A1 | 1/2006 |
| WO | WO 2006051704 A1 * | 5/2006 |
| WO | WO2008144360 A1 | 11/2008 |
| WO | WO2009114566 A1 | 9/2009 |
| WO | WO2010028338 A2 | 3/2010 |
| WO | WO2010071783 A1 | 6/2010 |

OTHER PUBLICATIONS

Lea W. Padgett "Recent developments in cannabinoid ligands" Life Sciences 2005, 77, 1767-1798.*
Arevalo-Martin, et al., "Therapeutic Action of Cannabinoids in a Murine Model of Multiple Sclerosis," Journal of Neuroscience, 2003, vol. 23 (7), pp. 2511-2516.
Benito, et al., "Cannabinoid CB2 Receptors and Fatty Acid Amide Hydrolase are Selectively Overexpressed in Neurotic Plaque-Associated Glia in Alzheimer's Disease Brains," Journal of Neuroscience, 2003, vol. 23 (35), pp. 11136-11141.
Bennett, et al., "A Peripheral Mononeuropathy in Rat that Produces Disorders of Pain Sensation like those Seen in Man," Pain, 1988, vol. 33 (1), pp. 87-107.
Berge, et al., "Pharmaceutical Salts," Journal of Pharmaceutical Sciences, 1977, vol. 66 (1), pp. 1-19.
Beylot, et al., "In Vivo Studies of Intrahepatic Metabolic Pathways," Diabetes Metabolism, 1997, vol. 23 (3), pp. 251-257.
Blagojevic, et al., "Role of heavy water in Boron Neutron Capture Therapy," Topics in Dosimetry & Treatment Planning for Neutron Capture Therapy, 1994, pp. 125-134.
Blake, et al., "Studies With Deuterated Drugs," Journal of Pharmaceutical Sciences, 1975, vol. 64 (3), pp. 367-391.
Bouchard, et al., "Contribution of Endocannabinoids in the Endothelial Protection Afforded by Ischemic Preconditioning in the Isolated Rat Heart," Life Sciences, 2003, vol. 72 (16), pp. 1859-1870.
Boyle, et al., "Osteoclast Differentiation and Activation," Nature, 2003, vol. 423 (6937), pp. 337-342.
Bozidar, et al., "Transformations of 1,2,4-Thiadiazolo/2,3-X/ Azines," Heterocycles, 1987, vol. 26 (3), pp. 689-697.
Bozidar, et al., "Transformations of 1-(2-Chloropyridy1-3)-4-ethoxycarbonyland 1-(2-Chloropyridy1-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
Brickner, et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

(Continued)

Primary Examiner — David K O Dell
(74) Attorney, Agent, or Firm — Lisa V. Mueller; Michael Best & Friedrich LLP

(57) ABSTRACT

The present invention provides for compounds of formula (I)

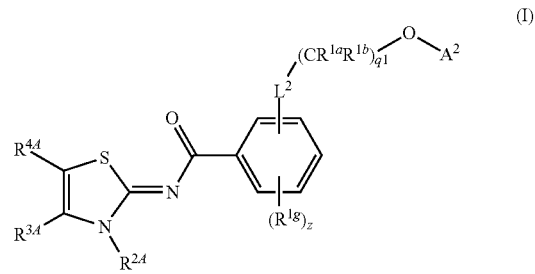

wherein $A^2$, $L^2$, $R^{1g}$, $R^{2A}$, $R^{3A}$, $R^{4A}$, $R^{1a}$, $R^{1b}$, q1, and z are as defined in the specification, are prodrugs of $CB_2$ receptors ligands and as such are useful in the prevention and treatment of various diseases and conditions including, but not limited to, pain.

22 Claims, No Drawings

(56) References Cited

OTHER PUBLICATIONS

Buckley, et al., "Immunomodulation by Cannabinoids is Absent in Mice Deficient for the Cannabinoid CB2 Receptor," European Journal of Pharmacology, 2000, vol. 396, pp. 141-149.

Carlisle, et al., "Differential Expression of the CB2 Cannabinoid Receptor by Rodent Macrophages and Macrophage-like Cells in Relation to Cell Activation," International Immunopharmacology, 2002, vol. 2, pp. 69.

Carrier, et al., "Endocannabinoids in Neuroimmunology and Stress," Current Drug Targets CNS and Neurological Disorders, 2005, vol. 4, pp. 657-665.

Casanova, et al., "Inhibition of Skin Tumor Growth and Angiogenesis in vivo by Activation of Cannabinoid Receptors," Journal of Clinical Investigation, 2003, vol. 111 (1), pp. 43-50.

Chaplan, et al., "Quantitative Assessment of Tactile Allodynia in the Rat Paw," Journal of Neuroscience Methods, 1994, vol. 53, pp. 55-63.

Cichewicz, "Synergistic Interactions Between Cannabinoid and Opioid Analgesics," Life Sciences, 2004, vol. 74 (11), pp. 1317-1324.

Clayton, et al., "CB1 and CB2 Cannabinoid Receptors are Implicated in Inflammatory Pain," Pain, 2002, vol. 96 (3), pp. 253-260.

Czajka, et al., "Effect of Deuterium Oxide on the Reproductive Potential of Mice," Annals of the New York Academy of Sciences, 1960, vol. 84, pp. 770-779.

Czajka, et al., "Physiological Effects of Deuterium on Dogs," American Journal of Physiology, 1961, vol. 201 (2), pp. 357-362.

Davidsen, et al., "N-(Acyloxyalkyl)pyridinium Salts as Soluble Prodrugs of a Potent Platelet Activating Factor Antagonist," Journal of Medicinal Chemistry, 1994, vol. 37 (26), pp. 4423-4429.

Dixon, "Efficient Analysis of Experimental Observations," Annual Review of Pharmacology and Toxicology, 1980, vol. 20, pp. 441-462.

Filippo, et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.

Foster, et al., "Deuterium Isotope Effects in the Metabolism of Drugs and Xenobiotics: Implications for Drug Design," Advances in Drug Research, 1985, vol. 14, pp. 2-36.

Galiégue, et al., "Expression of Central and Peripheral Cannabinoid Receptors in Human Immune Tissues and Leukocyte Subpopulations," European Journal of Biochemistry, 1995, vol. 232 (1), pp. 54-61.

Greene, et al., Protective Groups in Organic Synthesis, 3rd Edition, John Wiley and Sons, Inc., 1999, Table of Contents.

Grotenhermen, et al., "IACM 2nd Conference on Cannabinoids in Medicine," Expert Opinion in Pharmacotherapy, 1976, vol. 4 (12), pp. 2367-2371.

Hanus, et al., "HU-308: A Specific Agonist for CB 2, a Peripheral Cannabinoid Receptor," Proceedings of the National Academy of Science, 1999, vol. 96, pp. 14228-14233.

Hohmann, et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.

Ibrahim, et al., "Activation of CB2 Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.

Ibrahim, et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.

Ihenetu, et al., "Inhibition of Interleukin-8 Release in the Human Colonic Epithelial Cell Line HT-29 by Cannabinoids," European Journal of Pharmacology, 2003, vol. 458 (1-2), pp. 207-215.

International Search Report for Application No. PCT/US2010/060485, mailed Mar. 1, 2011, 4 pages.

Julien, et al., "Antifibrogenic Role of the Cannabinoid Receptor CB2 in the Liver," Gastroenterology, 2005, vol. 128, pp. 742-755.

Karsak, et al., "Cannabinoid Receptor Type 2 Gene is Associated with Human Osteoporosis," Human Molecular Genetics, 2005, vol. 14 (22), pp. 3389-3396.

Kato, et al., "Synthesis of Deuterated Mosapride Citrate," Journal of Labelled Compounds and Radiopharmaceuticals, 1995, vol. 36 (10), pp. 927-932.

Kim, et al., "An Experimental Model for Peripheral Neuropathy Produced by Segmental Spinal Nerve Ligation in the Rat," Pain, 1992, vol. 50 (3), pp. 355-363.

Kushner, et al., "Pharmacological uses and perspectives of heavy water and deuterated compounds," Canadian Journal of Physiology and Pharmacology, 1999, vol. 77 (2), pp. 79-88.

Lepicier, et al., "Endocannabinoids Protect the RAt Isolated Heart Against Ischaemia," British Journal of Pharmacology, 2003, vol. 139, pp. 805-815.

Lizondo, et al., "Linezolid: Oxazolidinone antibacterial," Drugs of the Future, 1996, vol. 21 (11), pp. 1116-1123.

Lotersztajn, et al., "Hepatic Fibrosis: Molecular Mechanisms and Drug Targets," Annual Review of Pharmacology and Toxicology, 2005, vol. 45, pp. 605-628.

Malan, et al., "CB2 Cannabinoid Receptor-Mediated Peripheral Antinociception," Pain, 2001, vol. 93, pp. 239-245.

Mallesham, et al., "Highly Efficient Cui-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Maresz, et al., "Modulation of the Cannabinoid CB2 Receptor in Microglial Cells in Response to Inflammatory Stimuli," Journal of Neurochemistry, 2005, vol. 95, pp. 437-445.

Mathison, et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.

McKallip, et al., "Targeting CB2 Cannabinoid Receptors as a Novel Therapy to Treat Malignant Lymphoblastic Disease," Blood, 2002, vol. 15 (2), pp. 627-634.

Nackley, et al., "Selective Activation of Cannabinoid CB2 Receptors Suppresses Spinal fos Protein Expression and Pain Behavior in a Rat Model of Inflammation," Neuroscience, 2003, vol. 119, pp. 747-757.

Ni, et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.

Patel, et al., "Inhibition of Guinea-Pig and Human Sensory Nerve Activity and the Cough Reflex in Guinea-Pigs by Cannabinoid (CB2) Receptor Activation," British Journal of Pharmacology, 2003, vol. 140 (2), pp. 261-268.

Pertwee, "Cannabinoids and Multiple Sclerosis," Pharmacology & Therapeutics, 2002, vol. 95, pp. 165-174.

Poste, et al., "Lipid Vesicles as Carriers for Introducing Biologically Active Materials into Cells," Methods in Cell Biology, 1976, vol. 14, pp. 33-71.

Quartilho, et al., "Inhibition of Inflammatory Hyperalgesia by Activation of Peripheral CB2 Cannabinoid Receptors," Anesthesiology, 2003, vol. 99, pp. 955-960.

Radulescu, et al., "Actes Du Colloque Franco-Roumain De Chimie Appliquee, 3rd, Bacau, Romania," 2004, pp. 117-120.

Radulescu, et al., "Synthesis and Characteristics of Compact Condensed Heterocyclic System 2-Aminothiazolo[5,4-c]Pyridine," Revista de Chimie, 2004, vol. 55 (11), pp. 889-893.

Radulescu, et al., "The Comparative Study on the Synthesis Methods of a Heterocyclic System 2-Aminothiazolo[4,5-13]Pyricline," Revista de Chimie, 2005, vol. 56 (6), pp. 659-662.

Ralston, "Regulation of Bone Mass, Bone Loss and Osteoclast Activity by Cannabinoid Receptors," Nature Medicine, 2005, vol. 11 (7), pp. 774-779.

Ramirez, et al., "Prevention of Alzheimers Disease Pathology by Cannabinoids: Neuroprotection Mediated by Blockade of Microglial Activation," Journal of Neuroscience, 2005, vol. 25 (8), pp. 1904-1913.

Sanchez, et al., "Inhibition of Glioma Growth in Vivo by Selective Activation of the CB2 Cannabinoid Receptor1," Cancer Research, 2001, vol. 61, pp. 5784-5789.

Shilpi, et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.

Steffens, et al., "Low Dose Oral Cannabinoid Therapy Reduces Progression of Atherosclerosis in Mice," Nature, 2005, vol. 434, pp. 782-786.

Thomson, "Physiological Effects of D20 in Mammals," Annals of the New York Academy of Sciences, 1960, vol. 84, pp. 736-744.

Valenzano, et al., "Pharmacological and Pharmacokinetic Characterization of the Cannabinoid Receptor 2 Agonist, Gw405833, Utilizing Rodent Models of Acute and Chronic Pain, Anxiety, Ataxia and Catalepsy," Neuropharmacology, 2005, vol. 48, pp. 658-672.

Warhurst, et al., "Interferon Gamma Induces Differential Upregulation of Alpha and Beta Chemokine Secretion in Colonic Epithelial Cell Lines," Gut, 1998, vol. 42 (2), pp. 208-213.

Wright, et al., "Differential Expression of Cannabinoid Receptors in the Human Colon: Cannabinoids Promote Epithelial Wound Healing," Gastroenterology, 2005, vol. 129 (2), pp. 437-453.

Yoshihara, et al., "Cannabinoid Receptor Agonists Inhibit Sensory Nerve Activation in Guinea Pig Airways," American Journal of Respiratory and Critical Care Medicine, 2004, vol. 170 (9), pp. 941-946.

Yoshihara, et al., "Endogenous Cannabinoid Receptor Agonists Inhibit Neurogenic Inflammations in Guinea Pig Airways," Allergy and Immunology, 2005, vol. 138, pp. 80-87.

Yoshihara, et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

\* cited by examiner

PRODRUG COMPOUNDS USEFUL AS CANNABINOID LIGANDS

CROSS REFERENCE TO RELATED APPLICATIONS

This application claims priority to U.S. application Ser. No. 61/286,845, filed Dec. 16, 2009, and is incorporated herein by reference in its entirety.

TECHNICAL FIELD

The present invention relates to prodrugs of potent and selective ligands of $CB_2$ receptors, which are useful in the treatment and prevention of various diseases and conditions.

BACKGROUND OF THE INVENTION (−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-operative pain) and bone fractures. Even though there can be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds presented herein are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

Selective $CB_2$ ligands have been disclosed in U.S. Patent Application Publication US2010/0216760.

SUMMARY OF THE INVENTION

The present invention relates to prodrugs of potent and selective ligands of $CB_2$ receptors, which are useful in the treatment and prevention of various diseases and conditions.

Compounds of formula (I) which are prodrugs of $CB_2$ ligands

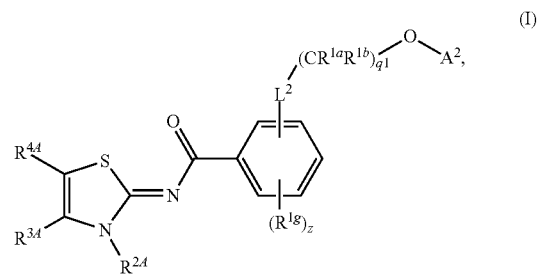

or pharmaceutically acceptable salts, solvates, or salts of solvates thereof, wherein $L^2$ is a bond, O, or $N(R^{bx})$; wherein $R^{bx}$ is hydrogen, alkyl, or haloalkyl;

$A^2$ is hydrogen, $-S(O)_2(OH)$, $-P(=O)(OH)(OH)$, $-(CR^{1e}R^{1f})_{q2}OP(=O)(OH)(OH)$, $-(CR^{1e}R^{1f})_{q2}OS(O)_2(OH)$, $-C(O)R^z$, $-C(O)(CR^{1c}R^{1d})_{q2}N(R^{aa})(R^{ab})$, $-C(O)O(CR^{1c}R^{1d})_{q4}N(R^{aa})(R^{ab})$, $-C(O)(CR^{1e}R^{1f})_{q2}C(O)OH$, $-C(O)(CR^{1e}R^{1f})_{q2}OP(=O)(OH)(OH)$, $-C(O)N(R^{aa})(-(CR^{1e}R^{1f})_{q4}-N(R^{ac})(R^{ad}))$, or $-C(O)(CR^{1e}R^{1f})_{q2}C(O)N(R^{aa})(R^{ab})$;

$R^z$ is alkyl, $G^{1a}$, or $-(CR^{1c}R^{1d})_{q2}G^{1a}$; wherein $G^{1a}$ is phenyl, monocyclic heteroaryl, monocyclic cycloalkyl, monocyclic cycloalkenyl, or monocyclic heterocycle;

$R^{ab}$, at each occurrence, is independently hydrogen, $C_1$-$C_6$ alkyl, haloalkyl, or $-(CR^{1e}R^{1f})_{q4}-N(R^{ac})(R^{ad})$;

each occurrence of $R^{1a}$, $R^{1b}$, $R^{1c}$, $R^{1e}$, $R^{1f}$, $R^{aa}$, $R^{ac}$, and $R^{ad}$, are each independently hydrogen, $C_1$-$C_6$ alkyl, or haloalkyl;

each occurrence of $R^{1d}$ is independently hydrogen, $C_1$-$C_6$ alkyl, haloalkyl, alkoxyalkyl, hydroxyalkyl, $-(CR^{1e}R^{1f})_{q3}-N(R^{ac})(R^{ad})$, or $-(CR^{1e}R^{1f})_{q3}-COOH$;

q1, q2, and q3, at each occurrence, are each independently 1, 2, 3, or 4;

$R^{2A}$ is $C_2$-$C_{10}$ alkyl, alkenyl, alkynyl, haloalkyl, $-(CR^{2a}R^{2b})_{q4}-OR^a$, $-(CR^{2a}R^{2b})_{q4}-O-G^{2a}$, $-(CR^{2a}R^{2b})_{q4}-O-(CR^{2c}R^{2d})_{q5}-O-R^a$, $-(CR^{2a}R^{2b})_{q4}-O-(CR^{2c}R^{2d})_{q5}-G^{2a}$, $-(CR^{2a}R^{2b})_{q4}-N(R^b)(R^c)$, $-(CR^{2a}R^{2b})_{q6}-C(O)-R^a$, $-(CR^{2a}R^{2b})_{q6}-SO_2-R^d$, $-(CR^{2a}R^{2b})_{q6}-G^{2a}$, or $-(CR^{2a}R^{2b})_{q6}-CN$;

$R^a$, $R^b$, and $R^c$, at each occurrence, are each independently hydrogen, alkyl, or haloalkyl;

$R^d$ is alkyl or haloalkyl;

$R^{2a}$, $R^{2b}$, $R^{2c}$, and $R^{2d}$, at each occurrence, are each independently hydrogen, halogen, $C_1$-$C_4$ haloalkyl, or $C_1$-$C_6$ alkyl;

q4, at each occurrence, is independently 2, 3, 4, or 5;

q5, at each occurrence, is independently 1, 2 or, 3;

q6, at each occurrence, are each independently 1, 2, 3, or 4;

$R^{3A}$ and $R^{4A}$ are the same or different, and are each independently $G^3$, hydrogen, alkyl, alkenyl, alkynyl, halogen, $-CN$, $-OR^h$, $-N(R^h)_2$, $-C(O)R^h$, $-C(O)O(R^h)$, haloalkyl, $-(CR^{3a}R^{3h})_{q6}-OR^h$; with the proviso that $A^2$ is other than hydrogen; or $R^{3A}$ and $R^{4A}$ together is

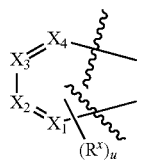

wherein $R^x$ is an optional substituent on one or more substitutable carbon atom, and each $R^x$ is independently selected from the group consisting of alkyl, halogen, hydroxy, alkoxy, haloalkoxy, and haloalkyl;

u is 0, 1, 2, or 3;

one or two of $X_1$, $X_2$, $X_3$, and $X_4$ is N or $N^+$-Q, and the others are CH; with the proviso that when $A^2$ is hydrogen, then at least one of $X_1$, $X_2$, $X_3$, and $X_4$ is $N^+$-Q;

Q is $O^-$, $-(CR^{qe}R^{qf})-OP(=O)(OH)(OH)$, $-(CR^{qe}R^{qf})-OS(O)_2(OH)$, $-(CR^{qe}R^{qf})-OC(O)R^p$, or formula (i)

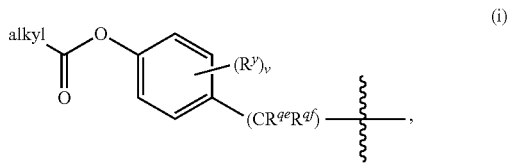

$R^p$ is alkyl, $N(R^q)(R^u)$, phenyl, monocyclic heterocycle, $-(CR^{qc}R^{qd})_{q7}-N(R^q)(R^u)$, $-N(R^q)(-(CR^{qe}R^{qf})_{q4}-N(R^q)(R^u))$, $-N(R^q)(-(CR^{qe}R^{qf})_{q4}-O(R^u))$, $-(CR^{qe}R^{qf})_{q7}-C(O)OH$, $-(CR^{qe}R^{qf})_{q7}-OP(=O)(OH)(OH)$, or $-(CR^{qc}R^{qd})_{q7}-C(O)N(R^q)(-(CR^{qe}R^{qf})_{q7}-N(R^q)(R^u))$, wherein the phenyl and the monocyclic heterocycle moieties are each independently unsubstituted or substituted with one or two substituents independently selected from the group consisting of alkyl, haloalkyl, OH, alkoxy, C(O)OH, C(O)O(alkyl), and halogen;

$R^y$ is alkyl;

v is 0, 1, 2, or 3;

each occurrence of $R^{3a}$, $R^{3b}$, $R^{qc}$, $R^{qe}$, $R^{qf}$, $R^q$, and $R^u$, are each independently hydrogen, $C_1$-$C_6$ alkyl, or haloalkyl;

each occurrence of $R^{qd}$ is independently hydrogen, $C_1$-$C_6$ alkyl, haloalkyl, alkoxyalkyl, hydroxyalkyl, $-(CR^{qe}R^{qf})_{q8}-N(R^q)(R^u)$, or $-(CR^{qe}R^{qf})_{q8}-COOH$;

q7 and q8, at each occurrence, are each independently 1, 2, or 3;

$G^3$ is monocyclic cycloalkyl or monocyclic heterocycle;

$G^{2a}$, at each occurrence, is independently a monocyclic ring selected from the group consisting of cycloalkyl, cycloalkenyl, heterocycle, phenyl, and heteroaryl;

each ring as represented by $G^3$, $G^{1a}$, and $G^{2a}$ is independently unsubstituted or substituted 1, 2, 3, 4, or 5 substituents independently selected from the group consisting of oxo, alkyl, halogen, hydroxy, alkoxy, $NH_2$, N(H)(alkyl), N(alkyl)$_2$, haloalkoxy, haloalkyl, $-(C_1$-$C_6$ alkylenyl)-$NH_2$, $-(C_1$-$C_6$ alkylenyl)-NH(alkyl), and $-(C_1$-$C_6$ alkylenyl)-N(alkyl)$_2$;

$R^{1g}$, at each occurrence, is independently $C_1$-$C_4$ alkyl, $C_2$-$C_4$ alkenyl, $C_2$-$C_4$ alkynyl, halogen, $C_1$-$C_4$ haloalkyl, $-CN$, $-OR^f$, $-OC(O)R^f$, $-OC(O)N(R^f)_2$, $-S(O)_2R^e$, $-S(O)_2N(R^f)_2$, $-C(O)R^f$, $-C(O)OR^f$, $-C(O)N(R^f)_2$, $-N(R^f)_2$, $-N(R^f)C(O)R^f$, $-N(R^f)S(O)_2R^e$, $-N(R^f)C(O)O(R^e)$, $-N(R)C(O)N(R^f)_2$, $-(CR^{2c}R^{2d})_{q3}-OR^f$, $-(CR^{2c}R^{2d})_{q3}-OC(O)R^f$, $-(CR^{2c}R^{2d})_{q3}-OC(O)N(R^f)_2$, $-(CR^{2c}R^{2d})_{q3}-S(O)_2R^e$, $-(CR^{2c}R^{2d})_{q3}-S(O)_2N(R^f)_2$, $-(CR^{2c}R^{2d})_{q3}-C(O)R^f$, $-(CR^{2c}R^{2d})_{q3}-C(O)OR^f$, $-(CR^{2c}R^{2d})_{q3}-C(O)N(R^f)_2$, $-(CR^{2c}R^{2d})_{q3}-N(R^f)_2$, $-(CR^{2c}R^{2d})_{q3}-N(R^f)C(O)R^f$, $-(CR^{2c}R^{2d})_{q3}-N(R^f)S(O)_2R^e$, $-(CR^{2c}R^{2d})_{q3}-N(R^f)C(O)O(R^e)$, $-(CR^{2c}R^{2d})_{q3}-N(R^f)C(O)N(R^f)_2$, or $-(CR^{2c}R^{2d})_{q3}-CN$;

$R^e$, at each occurrence, is independently $C_1$-$C_6$ alkyl or $C_1$-$C_4$ haloalkyl;

$R^f$ and $R^h$, at each occurrence, are each independently hydrogen, $C_1$-$C_6$ alkyl, or $C_1$-$C_4$ haloalkyl; and z is 0, 1, 2, 3, or 4; are disclosed herein.

Another aspect relates to pharmaceutical compositions comprising therapeutically effective amount of one or more compound(s) described herein or pharmaceutically acceptable salts, solvates, or salts of solvates thereof, in combination with one or more pharmaceutically acceptable carrier(s). Such compositions can be administered in accordance with methods described herein, typically as part of a therapeutic regimen for treatment or prevention of conditions and disorders related to cannabinoid (CB) receptor subtype $CB_2$. More particularly, the methods are useful for treating conditions related to pain such as, but not limited to, chronic pain, neuropathic pain, nociceptive pain, migraine, post-stroke pain, spinal cord injury, multiple sclerosis pain, osteoarthritic pain, inflammatory pain, cancer pain, lower back pain, post operative pain, diabetic neuropathic pain, fibromyalgia, post herpetic neuralgia, and eye pain; inflammatory disorders, immune disorders, neurological disorders, cancers of the immune system, respiratory disorders, obesity, diabetes, cardiovascular disorders, or for providing neuroprotection.

Further, provided herein are uses of the present compounds or pharmaceutically acceptable salts, solvates, or salts of solvates thereof, in the manufacture of medicaments for the treatment of the disease or conditions described above, alone or in combination with one or more pharmaceutically acceptable carrier(s), particularly for the treatment of pain such as, but not limited to, chronic pain, neuropathic pain, nociceptive pain, migraine, post-stroke pain, spinal cord injury, multiple sclerosis pain, osteoarthritric pain, inflammatory pain, cancer pain, lower back pain, post operative pain, diabetic neuropathic pain, fibromyalgia, post herpetic neuralgia, and eye pain, or combinations thereof.

The compounds, compositions comprising the compounds, pharmaceutically acceptable salts, solvates, or salts of the solvates thereof, and methods for treating or preventing conditions and disorders by administering the compounds or compositions thereof, are further described herein.

These and other objectives are described in the following paragraphs. These objectives should not be deemed to narrow the scope of the invention.

DETAILED DESCRIPTION OF THE INVENTION

Compounds of formula (I)

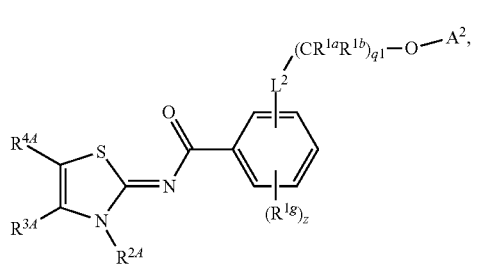

(I)

wherein $A^2$, $L^2$, $R^{1g}$, $R^{2A}$, $R^{3A}$, $R^{4A}$, $R^{1a}$, $R^{1b}$, q1, and z are as defined above in the Summary and below in the Detailed Description are disclosed. Compositions comprising such compounds and methods for treating conditions and disorders using such compounds and compositions are also disclosed.

In various embodiments, compounds described herein can contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH═CH— and —CH$_2$CH═CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylene group, as defined herein. Non-limiting examples of alkoxyalkyl include tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. For example "$C_1$-$C_6$ alkyl" means a straight or branched chain, saturated hydrocarbon containing 1 to 6 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain of 1 to 10 carbon atoms, for example, of 1 to 4 carbon atoms. The term "$C_1$-$C_6$ alkylenyl" means a divalent group derived from a straight or branched, saturated hydrocarbon chain of 1 to 6 carbon atoms. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group containing from 2 to 4 carbon atoms. Representative examples of alkynyl include, but are not limited to, acetylenyl, 1-propynyl, 2-propynyl, 3-butynyl, 2-pentynyl, and 1-butynyl.

The term "monocyclic cycloalkyl" means a monocyclic carbocyclic ring system containing three to eight carbon atoms, zero heteroatoms and zero double bonds. Examples of monocyclic cycloalkyls include cyclopropyl, cyclobutyl, cyclopentyl, cyclohexyl, cycloheptyl, and cyclooctyl. The monocyclic cycloalkyl rings can contain one or two alkylene bridges, each consisting of one, two, three, or four carbon atoms, each linking two non-adjacent carbon atoms of the ring system. Non-limiting examples of such bridged monocyclic cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic cycloalkyls can be unsubstituted or substituted, and are attached to the parent molecular moiety through any substitutable atom contained within the ring system.

The term "monocyclic cycloalkenyl" means a monocyclic hydrocarbon ring system having four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring can contain one or two alkylene bridges, each consisting of one, two, three, or four carbon atoms, each linking two non-adjacent carbon atoms of the ring system. The monocyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_4$ haloalkyl" means a $C_1$-$C_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloalkoxy" as used herein, means an alkoxy group, as defined herein, in which one, two, three, four, five or six hydrogen atoms are replaced by halogen. Non-limiting examples of haloalkoxy include 2-fluoroethoxy, 2,2,2-trifluoroethoxy, trifluoromethoxy, and difluoromethoxy.

The term "monocyclic heterocycle" or "monocyclic heterocyclic" as used herein, means a three-, four-, five-, six-, seven-, or eight-membered monocyclic ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Non-limiting examples of monocyclic heterocycles include azetidinyl (including, but not limited thereto, azetidin-2-yl), azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl (including, but not limited thereto, oxetan-2-yl), piperazinyl, piperidinyl, pyranyl, pyrazolinyl, pyrazolidinyl, pyrrolinyl, pyrrolidinyl (including, but not limited thereto, pyrrolidin-1-yl, pyrrolidin-2-yl, pyrrolidin-3-yl), tetrahydrofuranyl (including, but not limited thereto, tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The monocyclic heterocycles can contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings can optionally be oxidized and the nitrogen atoms can optionally be quarternized.

The term "monocyclic heteroaryl" as used herein, means a monocyclic five- or six-membered heteroaryl ring. The five-membered ring contains two double bonds and one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl. The monocyclic heteroaryl groups can be substituted or unsubstituted and are connected to the parent molecular moiety through any substitutable carbon atom or any substitutable nitrogen atom contained within the ring systems. The nitrogen and sulfur heteroatoms in the heteroaryl rings can optionally be oxidized and the nitrogen atoms can optionally be quarternized.

The term "heteroatom" as used herein, means a nitrogen, oxygen, or sulfur atom.

The term "hydroxyl" or "hydroxy" means a —OH group.

The term "hydroxyalkyl" as used herein, means a $C_2$-$C_6$ alkyl group, as defined herein, in which one or two hydrogen atoms are replaced by hydroxy groups.

The term "oxo" as used herein, means a =O group.

b. COMPOUNDS

Prodrugs of formula (I) are as described above.

Particular values of variable groups in compounds of formula (I) are as follows. Such values can be used where appropriate with any of the other values, definitions, claims or embodiments defined hereinbefore or hereinafter.

In one subset of formula (I) are compounds wherein the -$L^2$-$(CR^{1a}R^{1b})_{q1}$—O-$A^2$ functionality is situated on the ortho carbon atom of the phenyl ring. Thus, one embodiment is directed to a group of prodrugs of formula (II)

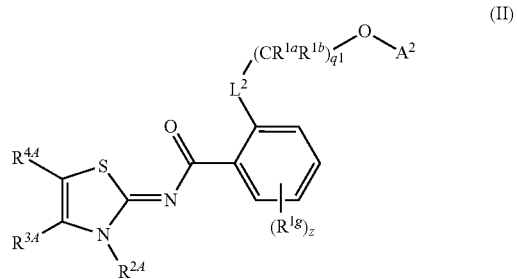

wherein $A^2$, $L^2$, $R^{1g}$, $R^{1a}$, $R^{1b}$, q1, $R^{2A}$, $R^{3A}$, $R^{4A}$, and z are as defined above in the Summary and the subsets or embodiments and combinations of the subsets and embodiments detailed below.

$R^{3A}$, $R^{4A}$, and $A^2$ have values as described generally in the Summary.

In one subset of formula (I) or (II) are compounds wherein $R^{3A}$ and $R^{4A}$ are each independently $G^3$, hydrogen, alkyl (for example, $C_1$-$C_4$ alkyl such as, but not limited to, methyl, ethyl, isopropyl, tert-butyl), alkenyl, alkynyl, —CN, halogen, —$OR^h$, —$N(R^h)_2$, —$C(O)R^h$, —$C(O)O(R^h)$, haloalkyl, or —$(CR^{3a}R^{3h})_{q6}$—$OR^h$. In one embodiment, $R^{3A}$ and $R^{4A}$ are each independently $G^3$, hydrogen, alkyl (for example, $C_1$-$C_4$ alkyl such as, but not limited to, methyl, ethyl, isopropyl, tert-butyl), alkenyl, alkynyl, halogen, haloalkyl, —C(O)O($R^h$), or —$(CR^{3a}R^{3h})_{q6}$—$OR^h$. In other embodiment, $R^{3A}$ and $R^{4A}$ are each independently $G^3$, hydrogen, or alkyl (for example, $C_1$-$C_4$ alkyl such as, but not limited to, methyl, ethyl, isopropyl, tert-butyl). Within these embodiments, $G^3$, $R^{3a}$, $R^{3h}$, q6, and $R^h$ are as described in the Summary and herein. $R^{3a}$ and $R^{ab}$ are, for example, each independently hydrogen or $C_1$-$C_6$ alkyl (such as, but not limited to, methyl). q6, for example, is 1 or 2. $R^h$, for example, is hydrogen or $C_1$-$C_6$ alkyl (e.g. methyl). Within certain embodiments, $R^h$ is hydrogen. In certain embodiments, $G^3$ is a monocyclic cycloalkyl (for example, but not limited thereto, cyclopropyl), optionally substituted as described generally in the Summary. In certain embodiments, $G^3$, for example, is 1-methylcyclopropyl. Examples of compounds of formula (I) and (II) include, but are not limited to, those wherein $R^{3A}$ and $R^{4A}$ are the same or different, and are each independently hydrogen or alkyl (for example, $C_1$-$C_4$ alkyl such as, but not limited to, methyl, ethyl, isopropyl, tert-butyl). In yet other embodiment, $R^{3A}$ is hydrogen and $R^{4A}$ is alkyl (for example, $C_1$-$C_4$ alkyl such as, but not limited to, methyl, ethyl, isopropyl, tert-butyl). In yet another embodiment, $R^{3A}$ is hydrogen and $R^{4A}$ is tert-butyl. In another embodiment, $R^{3A}$ and $R^{4A}$ are the same or different, and are each $C_1$-$C_4$ alkyl (for example, methyl). Within all these embodiments set forth, $A^2$ is —S(O)$_2$(OH), —P(=O)(OH)(OH), —(CR$^{1e}$R$^{1f}$)$_{q2}$OP(=O)(OH)(OH), —(CR$^{1e}$R$^{1f}$)$_{q2}$OS(O)$_2$(OH), —C(O)R$^z$, —C(O)(CR$^{1c}$R$^{1d}$)$_{q2}$N(R$^{aa}$)(R$^{ab}$), —C(O)O(CR$^{1c}$R$^{1d}$)$_{q4}$N(R$^{aa}$)(R$^{ab}$), —C(O)(CR$^{1e}$R$^{1f}$)$_{q2}$C(O)OH, —C(O)(CR$^{1e}$R$^{1f}$)$_{q2}$OP(=O)(OH)(OH), —C(O)N(R$^{aa}$)(—(CR$^{1e}$R$^{1f}$)$_{q4}$—N(R$^{ac}$)(R$^{ad}$)), or —C(O)(CR$^{1e}$R$^{1f}$)$_{q2}$C(O)N(R$^{aa}$)(R$^{ab}$). Certain examples of compounds of formula (I) or (II) include, but are not limited to those wherein $R^{3A}$ and $R^{4A}$ have values as described in this paragraph and $A^2$ is —P(=O)(OH)(OH), —C(O)R$^z$, —C(O)(CR$^{1c}$R$^{1d}$)$_{q2}$N(R$^{aa}$)(R$^{ab}$), —C(O)O(CR$^{1c}$R$^{1d}$)$_{q4}$N(R$^{aa}$)(R$^{ab}$), —C(O)(CR$^{1e}$R$^{1f}$)$_{q2}$C(O)OH, or —C(O)N(R$^{aa}$)(—(CR$^{1e}$R$^{1f}$)$_{q4}$—N(R$^{ac}$)(R$^{ad}$)). Other examples of compounds of formula (I) or (II) include, but are not limited to those wherein $R^{3A}$ and $R^{4A}$ have values as described in this paragraph and $A^2$ is —C(O)(CR$^{1c}$R$^{1d}$)$_{q2}$N(R$^{aa}$)(R$^{ab}$). R$^z$, R$^{1c}$, R$^{1d}$, R$^{1e}$, R$^{1f}$, R$^{aa}$, R$^{ab}$, R$^{ac}$, R$^{ad}$, q2, and q4 for all the above embodiments are as described in the Summary and examples herein below.

In another subset of formula (I) or (II) are compounds wherein $R^{3A}$ and $R^{4A}$, together is

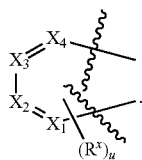

Thus, contemplated are compounds of formula (III) and (IV)

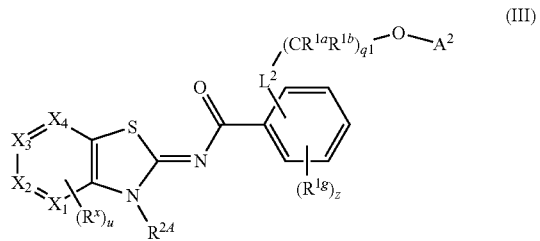

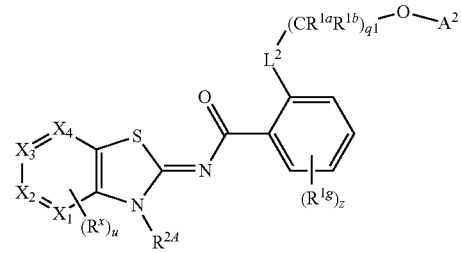

wherein $A^2$, $L^2$, $R^{1g}$, $R^{1a}$, $R^{1b}$, q1, $R^{2A}$, $R^x$, u, $X_1$, $X_2$, $X_3$, $X_4$, and z are as defined above in the Summary and the subsets, embodiments, and combinations of the subsets and embodiments detailed below.

In one subset of formula (III) or (IV) are compounds wherein one of $X_1$, $X_2$, $X_3$, and $X_4$ is N, and the others are CH, and $A^2$ is —S(O)$_2$(OH), —P(=O)(OH)(OH), —(CR$^{1e}$R$^{1f}$)$_{q2}$OP(=O)(OH)(OH), —(CR$^{1e}$R$^{1f}$)$_{q2}$OS(O)$_2$(OH), —C(O)R$^z$, —C(O)(CR$^{1c}$R$^{1d}$)$_{q2}$N(R$^{aa}$)(R$^{ab}$), —C(O)O(CR$^{1c}$R$^{1d}$)$_{q4}$N(R$^{aa}$)(R$^{ab}$), —C(O)(CR$^{1e}$R$^{1f}$)$_{q2}$C(O)OH, —C(O)(CR$^{1e}$R$^{1f}$)$_{q2}$OP(=O)(OH)(OH), —C(O)N(R$^{aa}$)(—(CR$^{1e}$R$^{1f}$)$_{q4}$—N(R$^{ac}$)(R$^{ad}$)), or —C(O)(CR$^{1e}$R$^{1f}$)$_{q2}$C(O)N(R$^{aa}$)(R$^{ab}$). In certain embodiment, one of $X_1$, $X_2$, $X_3$, and $X_4$ is N, and the others are CH, and $A^2$ is —P(=O)(OH)(OH), —C(O)R$^z$, —C(O)(CR$^{1c}$R$^{1d}$)$_{q2}$N(R$^{aa}$)(R$^{ab}$), —C(O)O(CR$^{1c}$R$^{1d}$)$_{q4}$N(R$^{aa}$)(R$^{ab}$), —C(O)(CR$^{1e}$R$^{1f}$)$_{q2}$C(O)OH, or —C(O)N(R$^{aa}$)(—(CR$^{1e}$R$^{1f}$)$_{q4}$—N(R$^{ac}$)(R$^{ad}$)). In certain embodiments, one of $X_1$, $X_2$, $X_3$, and $X_4$ is N, and the others are CH, and $A^2$ is —C(O)(CR$^{1c}$R$^{1d}$)$_{q2}$N(R$^{aa}$)(R$^{ab}$). Within these embodiments, R$^z$, R$^{1c}$, R$^{1d}$, R$^{1e}$, R$^{1f}$, R$^{aa}$, R$^{ab}$, R$^{ac}$, R$^{ad}$, q2, and q4 are as described in the Summary and embodiments herein below. Within the embodiment that one of $X_1$, $X_2$, $X_3$, and $X_4$ is N, and the others are CH, examples include those wherein $X_2$ is N and $X_1$, $X_3$, and $X_4$ are CH. Other examples include those wherein $X_4$ is N and $X_1$, $X_2$, and $X_3$ are CH.

Another subset is directed to compounds of formula (III) or (IV) wherein one of $X_1$, $X_2$, $X_3$, and $X_4$ is $N^+$-Q, and the others are CH, and $A^2$ is hydrogen. Q is as described in the Summary. In one embodiment, Q is $O^-$, —(CR$^{qe}$R$^{qf}$)—OC(O)R$^p$, or formula (i). In certain embodiments, Q is —(CR$^{qe}$R$^{qf}$)—OC(O)R$^p$, or formula (I). In yet other embodiments Q is —(CR$^{qe}$R$^{qf}$)—OC(O)R$^p$. In yet other embodiments, Q is formula (I). R$^{qe}$, R$^{qf}$, R$^p$, R$^y$, and v are as described in the Summary and embodiments herein. For example, in conjunction with any of the embodiments herein above or below, R$^{qe}$ and R$^{qf}$ are hydrogen. Within the embodiment that one of $X_1$, $X_2$, $X_3$, and $X_4$ is $N^+$-Q, and the others are CH, examples include those wherein $X_2$ is $N^+$-Q and $X_1$, $X_3$, and $X_4$ are CH. Other examples include those wherein $X_4$ is $N^+$-Q and $X_1$, $X_2$, and $X_3$ are CH. Within these embodiments, R$^p$, in conjunction with any above or below embodiments, for example, is alkyl (e.g. $C_1$-$C_4$ alkyl such as, but not limited to, methyl, tert-butyl), N(R$^q$)(R$^u$), —N(R$^q$)(—(CR$^{qe}$R$^{qf}$)$_{q4}$—O(R$^u$)), optionally substituted phenyl, or optionally substituted monocyclic heterocycle (e.g. optionally substituted pyrrolidinyl), wherein R$^q$, R$^u$, R$^{qe}$, R$^{qf}$, and q4 are as described in the Summary; for example, is alkyl (e.g $C_1$-$C_6$ alkyl such as, but not limited to, methyl, tert-butyl), N($C_1$-$C_6$ alkyl)$_2$, N(H)($C_1$-$C_6$ alkyl), optionally substituted phenyl, optionally substituted monocyclic heterocycle (e.g. optionally substituted pyrrolidinyl), or —N(H)(—(CH$_2$)$_{q4}$—O($C_1$-$C_6$ alkyl)) wherein q4 is 2, 3, or 4; R$^p$, for example, is optionally substituted phenyl.

$R^z$, $R^{1c}$, $R^{1d}$, $R^{1e}$, $R^{1f}$, $R^{aa}$, $R^{ab}$, $R^{ac}$, $R^{ad}$, q2, and q4 for the embodiments set forth above and below have values as described in the Summary and embodiments herein. $R^{1d}$, for example, is hydrogen, $C_1$-$C_6$ alkyl such as, but not limited to, methyl, or $(CR^{1e}R^{1f})_{q3}$—COOH. $R^{1e}$ and $R^{1f}$ are, for example, hydrogen. $R^{1c}$, $R^{aa}$, $R^{ab}$, $R^{ac}$, and $R^{ad}$, for example, are each independently hydrogen or $C_1$-$C_6$ alkyl such as, but not limited to, methyl. q2, for example, is 1 or 2. In certain embodiments, q2 is 1. In certain embodiments, q2 is 2. q4, for example, is 2 or 3. In certain embodiments, q4 is 2. $R^z$, for example, is alkyl (e.g. $C_1$-$C_6$ alkyl such as, but not limited to, methyl, ethyl, isopropyl), optionally substituted monocyclic heterocycle (e.g. optionally substituted pyrolidinyl), or —$(CR^{1c}R^{1d})_{q2}G^{1a}$ wherein $G^{1a}$ is optionally substituted monocyclic cycloalkyl.

$R^{2A}$ has values as described generally in the Summary. In one subset of formula (I), (II), (III), or (IV) are compounds wherein $R^{2A}$ is $C_2$-$C_{10}$ alkyl (e.g. $C_3$-$C_4$ alkyl such as but not limited to, isobutyl, n-butyl, n-propyl), alkenyl (e.g. but-2,3-dienyl), alkynyl (e.g. but-3-ynyl), haloalkyl (e.g. 3,3,3-trifluoropropyl, 4,4,4-trifluorobutyl), —$(CR^{2a}R^{2b})_{q4}$O—$R^a$, or —$(CR^{2a}R^{2b})_{q6}G^{2a}$. In one embodiment, $R^{2A}$ is $C_2$-$C_{10}$ alkyl (e.g. isobutyl, n-butyl, n-propyl, but not limited thereto), haloalkyl (e.g. 3,3,3-trifluoropropyl, 4,4,4-trifluorobutyl), or —$(CR^{2a}R^{2b})_{q6}$-$G^{2a}$. In other embodiment, $R^{2A}$ is $C_2$-$C_{10}$ alkyl (e.g. isobutyl, n-butyl, n-propyl, but not limited thereto) or haloalkyl (e.g. 3,3,3-trifluoropropyl, 4,4,4-trifluorobutyl). In yet other embodiment, $R^{2A}$ is —$(CR^{2a}R^{2b})_{q6}$-$G^{2a}$. In yet other embodiment, $R^{2A}$ is $C_2$-$C_{10}$ alkyl (e.g. isobutyl, n-butyl, n-propyl, but not limited thereto) or —$(CR^{2a}R^{2b})_{q6}$-$G^{2a}$. In a further embodiment, $R^{2A}$ is $C_2$-$C_{10}$ alkyl (e.g. isobutyl, n-butyl, n-propyl, but not limited thereto). Within all these embodiments, $R^{2a}$, $R^{2b}$, q4, q6, and $G^{2a}$ are as described in the Summary and herein. For example, $G^{2a}$ is an optionally substituted monocyclic ring selected from the group consisting of cycloalkyl, cycloalkenyl, heterocycle, phenyl, and heteroaryl. In certain embodiments, $G^{2a}$ is an optionally substituted monocyclic cycloalkyl (e.g. cyclopropyl, cyclobutyl, cyclopentyl, but not limited thereto) or optionally substituted monocyclic heterocycle (e.g. tetrahydrofuranyl). Each of these exemplified rings of $G^{2a}$ is independently unsubstituted or substituted as described in the Summary and herein. For example, each can be unsubstituted or substituted with 1 or 2 groups selected from alkyl such as, but not limited to, $C_1$-$C_4$ alkyl (e.g. methyl), halogen (e.g. F), haloalkyl, oxo, hydroxy, alkoxy (including, but not limited to $OCH_3$), and haloalkoxy. $R^{2a}$ and $R^{2b}$, for example, are each independently hydrogen or $C_1$-$C_6$ alkyl (e.g. methyl). In certain embodiments, $R^{2a}$ and $R^{2b}$ are hydrogen. q4, for example, is 2 or 3. q6, for example, is 1, 2, or 3. In certain embodiments wherein $R^{2A}$ is —$(CR^{2a}R^{2b})_{q6}$-$G^{2a}$, then $R^{2a}$ and $R^{2b}$ are hydrogen and q6 is 1.

$R^{1g}$ and z have values as described generally in the Summary. In certain subset of formula (I), (II), (III), or (IV) are compounds wherein $R^{1g}$ is $C_1$-$C_4$ alkyl, $C_2$-$C_4$ alkenyl, $C_2$-$C_4$ alkynyl, halogen, $C_1$-$C_4$ haloalkyl, —CN, or —$OR^f$ wherein $R^f$ is as disclosed in the Summary. In certain embodiments, $R^{1g}$ is halogen, $C_1$-$C_4$ haloalkyl (e.g. trifluoromethyl), or —CN. In certain embodiments, $R^{1g}$ is $C_1$-$C_4$ haloalkyl (e.g. trifluoromethyl). In certain embodiments, z is 0, 1, or 2. In yet other embodiments, z is 0 or 1. In certain embodiments, z is 1.

$L^2$ has values as described in the Summary. In certain subset of formula (I), (II), (III), or (IV) are compounds wherein $L^2$ is a bond. In other subset are compounds wherein $L^2$ is O. In yet other subset, $L^2$ is $N(R^{bx})$.

In certain subset of formula (I), (II), (III), or (IV) are compounds wherein $R^{1a}$ and $R^{1b}$ are the same or different, and are each independently hydrogen or $C_1$-$C_6$ alkyl (such as, but not limited to, methyl) and q1 is 2 or 3. In one embodiment, q1 is 2.

It is appreciated that the present invention contemplates compounds of formula (I), (II), (III), and (IV) with combinations of the above subsets and embodiments, including particular, more particular and preferred embodiments.

Accordingly, one aspect is directed to a group of compounds of formula (I), (II), (III), or (IV) wherein $L^2$ is O and $R^{2A}$ is $C_2$-$C_{10}$ alkyl (e.g. isobutyl, n-butyl, n-propyl, but not limited thereto) or haloalkyl.

Another aspect is directed to a group of compounds of formula (I), (II), (III), or (IV) wherein $L^2$ is O and $R^{2A}$ is $C_2$-$C_{10}$ alkyl (e.g. isobutyl, n-butyl, n-propyl, but not limited thereto).

Another aspect is directed to a group of compounds of formula (I), (II), (III), or (IV) wherein $L^2$ is O and $R^{2A}$ is n-butyl.

Yet another aspect is directed to a group of compounds of formula (I), (II), (III), or (IV) wherein one of $X_1$, $X_2$, $X_3$, and $X_4$ is N, and the others are CH, $A^2$ is —P(=O)(OH)(OH), —C(O)$R^z$, —C(O)$(CR^{1c}R^{1d})_{q2}N(R^{aa})(R^{ab})$, —C(O)O$(CR^{1c}R^{1d})_{q4}N(R^{aa})(R^{ab})$, —C(O)$(CR^{1e}R^{1f})_{q2}C(O)OH$, or —C(O)$N(R^{aa})(-(CR^{1e}R^{1f})_{q4}-N(R^{ac})(R^{ad}))$, and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein one of $X_1$, $X_2$, $X_3$, and $X_4$ is N, and the others are CH, $A^2$ is —P(=O)(OH)(OH), —C(O)$R^z$, —C(O)$(CR^{1c}R^{1d})_{q2}N(R^{aa})(R^{ab})$, —C(O)O$(CR^{1c}R^{1d})_{q4}N(R^{aa})(R^{ab})$, —C(O)$(CR^{1e}R^{1f})_{q2}C(O)OH$, or —C(O)$N(R^{aa})(-(CR^{1e}R^{1f})_{q4}-N(R^{ac})(R^{ad}))$, and $R^{2A}$ is $C_2$-$C_{10}$ alkyl (e.g. isobutyl, n-butyl, n-propyl, but not limited thereto).

Yet another aspect is directed to a group of compounds of formula (I), (II), (III), or (IV) wherein $X_2$ is N, $X_1$, $X_3$, and $X_4$ are CH, $A^2$ is —P(=O)(OH)(OH), —C(O)$R^z$, —C(O)$(CR^{1c}R^{1d})_{q2}N(R^{aa})(R^{ab})$, —C(O)O$(CR^{1c}R^{1d})_{q4}N(R^{aa})(R^{ab})$, —C(O)$(CR^{1e}R^{1f})_{q2}C(O)OH$, or —C(O)$N(R^{aa})(-(CR^{1e}R^{1f})_{q4}-N(R^{ac})(R^{ad}))$, and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein $X_2$ is N, $X_1$, $X_3$, and $X_4$ are CH, $A^2$ is —P(=O)(OH)(OH), —C(O)$R^z$, —C(O)$(CR^{1c}R^{1d})_{q2}N(R^{aa})(R^{ab})$, —C(O)O$(CR^{1c}R^{1d})_{q4}N(R^{aa})(R^{ab})$, —C(O)$(CR^{1e}R^{1f})_{q2}C(O)OH$, or —C(O)$N(R^{aa})(-(CR^{1e}R^{1f})_{q4}-N(R^{ac})(R^{ad}))$, and $R^{2A}$ is $C_2$-$C_{10}$ alkyl (e.g. isobutyl, n-butyl, n-propyl, but not limited thereto).

Yet another aspect is directed to a group of compounds of formula (I), (II), (III), or (IV) wherein $X_4$ is N, $X_1$, $X_2$, and $X_3$ are CH, $A^2$ is —P(=O)(OH)(OH), —C(O)$R^z$, —C(O)$(CR^{1c}R^{1d})_{q2}N(R^{aa})(R^{ab})$, —C(O)O$(CR^{1c}R^{1d})_{q4}N(R^{aa})(R^{ab})$, —C(O)$(CR^{1e}R^{1f})_{q2}C(O)OH$, or —C(O)$N(R^{aa})(-(CR^{1e}R^{1f})_{q4}-N(R^{ac})(R^{ad}))$, and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein $X_4$ is N, $X_1$, $X_2$, and $X_3$ are CH, $A^2$ is —P(=O)(OH)(OH), —C(O)$R^z$, —C(O)$(CR^{1c}R^{1d})_{q2}N(R^{aa})(R^{ab})$, —C(O)O$(CR^{1c}R^{1d})_{q4}N(R^{aa})(R^{ab})$, —C(O)$(CR^{1e}R^{1f})_{q2}C(O)OH$, or —C(O)$N(R^{aa})(-(CR^{1e}R^{1f})_{q4}-N(R^{ac})(R^{ad}))$, and $R^{2A}$ is $C_2$-$C_{10}$ alkyl (e.g. isobutyl, n-butyl, n-propyl, but not limited thereto).

Another aspect is directed to a group of compounds of formula (I), (II), (III), or (IV) wherein one of $X_1$, $X_2$, $X_3$, and $X_4$ is N, and the others are CH, $A^2$ is —C(O)$(CR^{1c}R^{1d})_{q2}N$ ($R^{aa}$)($R^{ab}$), and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein one of $X_1$, $X_2$, $X_3$, and $X_4$ is N, and the others are CH, $A^2$ is —C(O)($CR^{1c}R^{1d}$)$_{q2}$N($R^{aa}$)($R^{ab}$), and $R^{2A}$ is $C_2$-$C_{10}$ alkyl (e.g. isobutyl, n-butyl, n-propyl, but not limited thereto).

Another aspect is directed to a group of compounds of formula (I), (II), (III), or (IV) wherein $X_2$ is N, $X_1$, $X_3$, and $X_4$ are CH, $A^2$ is —C(O)($CR^{1c}R^{1d}$)$_{q2}$N($R^{aa}$)($R^{ab}$), and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein $X_2$ is N, $X_1$, $X_3$, and $X_4$ are CH, $A^2$ is —C(O)($CR^{1c}R^{1d}$)$_{q2}$N($R^{aa}$)($R^{ab}$), and $R^{2A}$ is $C_2$-$C_{10}$ alkyl (e.g. isobutyl, n-butyl, n-propyl, but not limited thereto).

Another aspect is directed to a group of compounds of formula (I), (II), (III), or (IV) wherein $X_4$ is N, $X_1$, $X_2$, and $X_3$ are CH, $A^2$ is —C(O)($CR^{1c}R^{1d}$)$_{q2}$N($R^{aa}$)($R^{ab}$), and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein $X_4$ is N, $X_1$, $X_2$, and $X_3$ are CH, $A^2$ is —C(O)($CR^{1c}R^{1d}$)$_{q2}$N($R^{aa}$)($R^{ab}$) and $R^{2A}$ is $C_2$-$C_{10}$ alkyl (e.g. isobutyl, n-butyl, n-propyl, but not limited thereto).

Yet another aspect is directed to a group of compounds of formula (I), (II), (III), or (IV) wherein one of $X_1$, $X_2$, $X_3$, and $X_4$ is $N^+$-Q, and the others are CH, $A^2$ is hydrogen, and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein one of $X_1$, $X_2$, $X_3$, and $X_4$ is $N^+$-Q, and the others are CH, $A^2$ is hydrogen, and $R^{2A}$ is $C_2$-$C_{10}$ alkyl (e.g. isobutyl, n-butyl, n-propyl, but not limited thereto).

Yet another aspect is directed to a group of compounds of formula (I), (II), (III), or (IV) wherein $X_2$ is $N^+$-Q, $X_1$, $X_3$, and $X_4$ are CH, $A^2$ is hydrogen, and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein $X_2$ is $N^+$-Q, $X_1$, $X_3$, and $X_4$ are CH, $A^2$ is hydrogen, and $R^{2A}$ is $C_2$-$C_{10}$ alkyl (e.g. isobutyl, n-butyl, n-propyl, but not limited thereto).

Yet another aspect is directed to a group of compounds of formula (I), (II), (III), or (IV) wherein $X_4$ is $N^+$-Q, $X_1$, $X_2$, and $X_3$ are CH, $A^2$ is hydrogen, and $R^{2A}$ is $C_2$-$C_{10}$ alkyl (e.g. isobutyl, n-butyl, n-propyl, but not limited thereto) or haloalkyl.

Yet another aspect is directed to a group of compounds of formula (I), (II), (III), or (IV) wherein $X_4$ is $N^+$-Q, $X_1$, $X_2$, and $X_3$ are CH, $A^2$ is hydrogen, and $R^{2A}$ is $C_2$-$C_{10}$ alkyl (e.g. isobutyl, n-butyl, n-propyl, but not limited thereto).

Another aspect is directed to a group of compounds of formula (I), (II), (III), or (IV) wherein one of $X_1$, $X_2$, $X_3$, and $X_4$ is $N^+$-Q, and the others are CH, $A^2$ is hydrogen, Q is $O^-$, —($CR^{qe}R^{qf}$)—OC(O)$R^p$, or formula (I), and $R^{2A}$ is $C_2$-$C_{10}$ alkyl (e.g. isobutyl, n-butyl, n-propyl, but not limited thereto) or haloalkyl. In certain embodiments, Q is —($CR^{qe}R^{qf}$)—OC(O)$R^p$ or formula (i).

Yet another aspect is directed to a group of compounds of formula (I), (II), (III), or (IV) wherein one of $X_1$, $X_2$, $X_3$, and $X_4$ is $N^+$-Q, and the others are CH, $A^2$ is hydrogen, Q is $O^-$, —($CR^{qe}R^{qf}$)—OC(O)$R^p$, or formula (I), and $R^{2A}$ is $C_2$-$C_{10}$ alkyl (e.g. isobutyl, n-butyl, n-propyl, but not limited thereto). In certain embodiments, Q is —($CR^{qe}R^{qf}$)—OC(O)$R^p$ or formula (i).

Another aspect is directed to a group of compounds of formula (I), (II), (III), or (IV) wherein $X_2$ is $N^+$-Q, $X_1$, $X_3$, and $X_4$ are CH, $A^2$ is hydrogen, Q is $O^-$, —($CR^{qe}R^{qf}$)—OC(O)$R^p$, or formula (i), and $R^{2A}$ is $C_2$-$C_{10}$ alkyl (e.g. isobutyl, n-butyl, n-propyl, but not limited thereto) or haloalkyl. In certain embodiments, Q is —($CR^{qe}R^{qf}$)—OC(O)$R^p$ or formula (i).

Yet another aspect is directed to a group of compounds of formula (I), (II), (III), or (IV) wherein $X_2$ is $N^+$-Q, $X_1$, $X_3$, and $X_4$ are CH, $A^2$ is hydrogen, Q is $O^-$, —($CR^{qe}R^{qf}$)—OC(O)$R^p$, or formula (I), and $R^{2A}$ is $C_2$-$C_{10}$ alkyl (e.g. isobutyl, n-butyl, n-propyl, but not limited thereto). In certain embodiments, Q is —($CR^{qe}R^{qf}$)—OC(O)$R^p$ or formula (i).

Another aspect is directed to a group of compounds of formula (I), (II), (III), or (IV) wherein $X_4$ is $N^+$-Q, $X_1$, $X_2$, and $X_3$ are CH, $A^2$ is hydrogen, Q is $O^-$, —($CR^{qe}R^{qf}$)—OC(O)$R^p$, or formula (i), and $R^{2A}$ is $C_2$-$C_{10}$ alkyl (e.g. isobutyl, n-butyl, n-propyl, but not limited thereto) or haloalkyl. In certain embodiments, Q is —($CR^{qe}R^{qf}$)—OC(O)$R^p$ or formula (i).

Yet another aspect is directed to a group of compounds of formula (I), (II), (III), or (IV) wherein $X_4$ is $N^+$-Q, $X_1$, $X_2$, and $X_3$ are CH, $A^2$ is hydrogen, Q is $O^-$, —($CR^{qe}R^{qf}$)—OC(O)$R^p$, or formula (I), and $R^{2A}$ is $C_2$-$C_{10}$ alkyl (e.g. isobutyl, n-butyl, n-propyl, but not limited thereto). In certain embodiments, Q is —($CR^{qe}R^{qf}$)—OC(O)$R^p$ or formula (i).

Another aspect is directed to a group of compounds of formula (I), (II), (III), or (IV) wherein one of $X_1$, $X_2$, $X_3$, and $X_4$ is $N^+$-Q, and the others are CH, $A^2$ is hydrogen, Q is —($CR^{qe}R^{qf}$)—OC(O)$R^p$, and $R^{2A}$ is $C_2$-$C_{10}$ alkyl (e.g. isobutyl, n-butyl, n-propyl, but not limited thereto) or haloalkyl. In one embodiment, $R^p$ is optionally substituted phenyl.

Yet another aspect is directed to a group of compounds of formula (I), (II), (III), or (IV) wherein one of $X_1$, $X_2$, $X_3$, and $X_4$ is $N^+$-Q, and the others are CH, $A^2$ is hydrogen, Q is —($CR^{qe}R^{qf}$)—OC(O)$R^p$, and $R^{2A}$ is $C_2$-$C_{10}$ alkyl (e.g. isobutyl, n-butyl, n-propyl, but not limited thereto). In one embodiment, $R^p$ is optionally substituted phenyl.

Another aspect is directed to a group of compounds of formula (I), (II), (III), or (IV) wherein $X_2$ is $N^+$-Q, $X_1$, $X_3$, and $X_4$ are CH, $A^2$ is hydrogen, Q is —($CR^{qe}R^{qf}$)—OC(O)$R^p$, and $R^{2A}$ is $C_2$-$C_{10}$ alkyl (e.g. isobutyl, n-butyl, n-propyl, but not limited thereto) or haloalkyl. In one embodiment, $R^p$ is optionally substituted phenyl.

Yet another aspect is directed to a group of compounds of formula (I), (II), (III), or (IV) wherein $X_2$ is $N^+$-Q, $X_1$, $X_3$, and $X_4$ are CH, $A^2$ is hydrogen, Q is —($CR^{qe}R^{qf}$)—OC(O)$R^p$, and $R^{2A}$ is $C_2$-$C_{10}$ alkyl (e.g. isobutyl, n-butyl, n-propyl, but not limited thereto). In one embodiment, $R^p$ is optionally substituted phenyl.

Another aspect is directed to a group of compounds of formula (I), (II), (III), or (IV) wherein $X_4$ is $N^+$-Q, $X_1$, $X_2$, and $X_3$ are CH, $A^2$ is hydrogen, Q is —($CR^{qe}R^{qf}$)—OC(O)$R^p$, and $R^{2A}$ is $C_2$-$C_{10}$ alkyl (e.g. isobutyl, n-butyl, n-propyl, but not limited thereto) or haloalkyl. In one embodiment, $R^p$ is optionally substituted phenyl.

Yet another aspect is directed to a group of compounds of formula (I), (II), (III), or (IV) wherein $X_4$ is $N^+$-Q, $X_1$, $X_2$, and $X_3$ are CH, $A^2$ is hydrogen, Q is —($CR^{qe}R^{qf}$)—OC(O)$R^p$, and $R^{2A}$ is $C_2$-$C_{10}$ alkyl (e.g. isobutyl, n-butyl, n-propyl, but not limited thereto). In one embodiment, $R^p$ is optionally substituted phenyl.

Within each group of compounds of formula (I), (II), (III), or (IV) described above, $R^{1a}$, $R^{1b}$, q1, $R^{1g}$, z, $R^x$, u, and $L^2$ have meanings as disclosed in the Summary and embodiments herein above.

Thus, within each group of compounds of formula (I), (II), (III), or (IV) described above, examples of a subgroup include, but are not limited to, those wherein $L^2$ is O.

Examples of another subgroup include, but are not limited to, those wherein $L^2$ is O, $R^{1a}$ and $R^{1b}$, at each occurrence, are each independently hydrogen or $C_1$-$C_6$ alkyl, and q1 is 2.

Examples of another subgroup include, but are not limited to, those wherein $L^2$ is O, $R^{1a}$ and $R^{1b}$, at each occurrence, are each independently hydrogen or $C_1$-$C_6$ alkyl, q1 is 2, and u is 0.

Examples of another subgroup include, but are not limited to, those wherein L² is O, R¹ᵃ and R¹ᵇ, at each occurrence, are each independently hydrogen or $C_1$-$C_6$ alkyl, q1 is 2, u is 0, and R¹ᵍ is halogen, $C_1$-$C_4$ haloalkyl (e.g. trifluoromethyl), or —CN.

Examples of another subgroup include, but are not limited to, those wherein L² is O, R¹ᵃ and R¹ᵇ, at each occurrence, are each independently hydrogen or $C_1$-$C_6$ alkyl, q1 is 2, u is 0, and R¹ᵍ is $C_1$-$C_4$ haloalkyl (e.g. trifluoromethyl).

Examples of another subgroup include, but are not limited to, those wherein L² is N(Rᵇˣ).

Examples of another subgroup include, but are not limited to, those wherein L² is N(Rᵇˣ), R¹ᵃ and R¹ᵇ, at each occurrence, are each independently hydrogen or $C_1$-$C_6$ alkyl, and q1 is 2.

Examples of another subgroup include, but are not limited to, those wherein L² is N(Rᵇˣ), R¹ᵃ and R¹ᵇ, at each occurrence, are each independently hydrogen or $C_1$-$C_6$ alkyl, q1 is 2, and u is O.

Examples of another subgroup include, but are not limited to, those wherein L² is N(Rᵇˣ), R¹ᵃ and R¹ᵇ, at each occurrence, are each independently hydrogen or $C_1$-$C_6$ alkyl, q1 is 2, u is 0, and R¹ᵍ is halogen, $C_1$-$C_4$ haloalkyl (e.g. trifluoromethyl), or —CN.

Exemplary compounds include, but are not limited to:
(2Z)-5-[(acetyloxy)methyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium;
(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-methylalaninate;
(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl glycinate;
(2Z)-3-butyl-5-{[(2,2-dimethylpropanoyl)oxy]methyl}-2-{[2-{[(2S)-2-hydroxypropyl]oxy}-5-(trifluoromethyl)benzoyl]imino}-2,3-dihydro[1,3]thiazolo[4,5-c]pyridin-5-ium;
(2Z)-5-[(benzoyloxy)methyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium;
(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl L-alaninate;
(2Z)-3-butyl-2-{[2-{[(2S)-2-hydroxypropyl]oxy}-5-(trifluoromethyl)benzoyl]imino}-5-[({[(2S)-2-(methoxycarbonyl)pyrrolidin-1-yl]carbonyl}oxy)methyl]-2,3-dihydro[1,3]thiazolo[4,5-c]pyridin-5-ium;
(2Z)-3-butyl-5-({[(dimethylamino)carbonyl]oxy}methyl)-2-{[2-{[(2S)-2-hydroxypropyl]oxy}-5-(trifluoromethyl)benzoyl]imino}-2,3-dihydro[1,3]thiazolo[4,5-c]pyridin-5-ium;
(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl dihydrogen phosphate;
(2Z)-3-butyl-2-{[2-{[(2S)-2-hydroxypropyl]oxy}-5-(trifluoromethyl)benzoyl]imino}-5-[({[(3-methoxypropyl)amino]carbonyl}oxy)methyl]-2,3-dihydro[1,3]thiazolo[4,5-c]pyridin-5-ium;
(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl N-methylglycinate;
N-[(2Z)-3-butyl-5-oxido[1,3]thiazolo[4,5-c]pyridin-2(3H)-ylidene]-2-{[(2S)-2-hydroxypropyl]oxy}-5-(trifluoromethyl)benzamide;
(2Z)-5-[4-(acetyloxy)-3,5-dimethylbenzyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium;
4-({(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl}oxy)-4-oxobutanoic acid;
(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-(dimethylamino)ethylcarbamate;
(3S)-4-({(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl}oxy)-3-amino-4-oxobutanoic acid;
(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-(dimethylamino)ethyl carbonate;
(2S)-1-[2-{[(2Z)-3-butyl[1,3]thiazolo[4,5-c]pyridin-2(3H)-ylidene]carbamoyl}-4-(trifluoromethyl)phenoxy]propan-2-yl L-prolinate;
(2S)-1-[2-{[(2Z)-3-butyl[1,3]thiazolo[4,5-c]pyridin-2(3H)-ylidene]carbamoyl}-4-(trifluoromethyl)phenoxy]propan-2-yl D-alaninate;
(2S)-1-[2-{[(2Z)-3-butyl[1,3]thiazolo[4,5-c]pyridin-2(3H)-ylidene]carbamoyl}-4-(trifluoromethyl)phenoxy]propan-2-yl[1-(aminomethyl)cyclohexyl]acetate;
(2S)-1-[2-{[(2Z)-3-butyl[1,3]thiazolo[4,5-c]pyridin-2(3H)-ylidene]carbamoyl}-4-(trifluoromethyl)phenoxy]propan-2-yl acetate; and
(2R)-1-[2-{[(2Z)-3-butyl[1,3]thiazolo[4,5-c]pyridin-2(3H)-ylidene]carbamoyl}-4-(trifluoromethyl)phenoxy]propan-2-yl D-alaninate;

or pharmaceutically acceptable salts, solvates, or salts of solvates thereof.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers of various ratios, including racemic mixtures. The above formula (I), (II), (III), and (IV) are shown without a definitive stereochemistry at certain positions. It is understood that all stereoisomers of formula (I), (II), (III), and (IV) and mixtures thereof, and their pharmaceutically acceptable salts, solvates, and salts of solvates thereof are included in this application. Individual stereoisomers can be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. Various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein can exhibit the phenomenon of tautomerism. Example includes a ketone and its enol form known as keto-enol tautomers.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of $CB_2$ ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.,* 36(10):927-932 (1995); Kushner et al., *Can. J. Physiol. Pharmacol.,* 77, 79-88 (1999).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physico-chemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions potentially altering the pharmcokinetic profile or efficacy relative to the non-isotopic compound.

c. METHODS OF USING THE COMPOUNDS

Compounds disclosed herein are prodrugs of potent and selective ligands of $CB_2$ receptors, and as such are useful in the treatment and prevention of various diseases and conditions in mammals, preferably human.

Thus one aspect provides a method for the prevention and treatment of various diseases and conditions in a mammal which comprises administering to said mammal a therapeutically effective amount of one or more compounds of formula (I), (II), (III), or (IV), with or without one or more pharmaceutically acceptable carrier(s). This aspect encompasses the use of one or more compounds of formula (I), (II), (III), or (IV) for the manufacture of medicament for the treatment or prevention of various diseases and conditions. One embodiment provides methods for treating pain (for example, chronic pain, neuropathic pain, nociceptive pain, migraine, post-stroke pain, spinal cord injury, multiple sclerosis pain, osteoarthritric pain, inflammatory pain, cancer pain, lower back pain, post operative pain, diabetic neuropathic pain, migraine, fibromyalgia, post herpatic neuralgia, phantom limb pain, and eye pain, or combinations thereof) in a mammal (including human) in need of such treatment. The methods comprise administering to the mammal therapeutically effective amount of one or more compounds as described herein, or pharmaceutically acceptable salts, solvates, or salts of solvates thereof, alone or in combination with one or more pharmaceutically acceptable carrier(s). The method further comprises administration of the present compounds as a single dose. The method also comprises repeated or chronic administration of the present compounds over a period of days, weeks, months, or longer. In certain embodiments, the method comprises administering to the mammal a therapeutically effective amount of any of the compounds as described herein, or a pharmaceutically acceptable salt, solvate, or salt of a solvate thereof, in combination with one or more nonsteroidal anti-inflammatory drugs (NSAIDs), or other analgesics (for example, acetaminophen, opioids, etc.), or combinations thereof.

Another embodiment provides methods for treating disorders selected from the group consisting of inflammatory disorders, immune disorders, neurological disorders, cancers of the immune system, respiratory disorders, and cardiovascular disorders in a mammal in need of such treatment. The method comprises administering to the mammal therapeutically effective amount of one or more compounds described herein or pharmaceutically acceptable salts, solvates, or salts of solvates thereof, alone or in combination with one or more pharmaceutically acceptable carrier(s).

Yet another embodiment relates to methods for providing neuroprotection in a mammal in need of such treatment. These methods comprise administering to the mammal therapeutically effective amounts of one or more compounds described herein or pharmaceutically acceptable salts, solvates, or salts of solvates thereof, alone or in combination with one or more pharmaceutically acceptable carrier(s).

Another embodiment provides method for increasing the therapeutic effectiveness or potency of compounds described herein by repeated or chronic administration over a period of days, weeks, or months.

Several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators can be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands can be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators can provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators can possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators can represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators can represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators can have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators can be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor can be clinically useful for the treatment of atheroscelorsis.

$CB_2$ receptors are expressed on malignant cells of the immune system and targeting $CB_2$ receptors to induce apoptosis can constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators can have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators can have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level can depend upon the activity of the particular compound, the route of administration, the duration of treatment, the severity of the condition being treated and the condition and prior medical history of the patient being treated. The dose can also vary according to the age, weight, and response of the individual patient. However, it is within the skill of the art to start doses of the compound at levels lower than required to achieve the desired therapeutic effect and to gradually increase the dosage until the desired effect is achieved. In the treatment of certain medical conditions, repeated or chronic administration of the compounds can be required to achieve the desired therapeutic response. "Repeated or chronic administration" refers to the administration of the compounds daily (i.e., every day) or intermittently (i.e., not every day) over a period of days, weeks, months, or longer. In particular, the treatment of chronic painful conditions is anticipated to require such repeated or chronic administration of compounds described herein. The compounds can become more effective upon repeated or chronic administration such that the therapeutically effective doses on repeated or chronic administration can be lower than the therapeutically effective dose from a single administration.

Compounds can also be administered as a pharmaceutical composition comprising the compounds of interest, or pharmaceutically acceptable salts, solvates, or salts of solvates thereof, in combination with one or more pharmaceutically acceptable carriers. The phrase "therapeutically effective amount" of a compound means a sufficient amount of the compound to treat disorders, at a reasonable benefit/risk ratio applicable to any medical treatment. It can be understood, however, that the total daily usage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The compounds can be administered alone, or in combination with one or more other compounds described herein, or in combination (i.e. co-administered) with one or more additional pharmaceutical agents. For example, one or more compounds, or pharmaceutically acceptable salts, solvates, or salts of solvates thereof, can be administered in combination with one or more analgesic (e.g. acetaminophen, opioid such as morphine), or with one or more nonsteroidal anti-inflammatory drugs (NSAIDs), or combinations thereof. Non-limiting examples of NSAIDs include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent, in its own separate pharmaceutical dosage formulation. For example, one or more compounds described herein and one or more additional pharmaceutical agents, can be administered to the patient together, in a single oral dosage composition having a fixed ratio of each active ingredient, such as a tablet or capsule; or each agent can be administered in separate oral dosage formulations.

Where separate dosage formulations are used, the compounds and one or more additional pharmaceutical agents can be administered at essentially the same time (e.g., concurrently) or at separately staggered times (e.g., sequentially).

In general, the total daily dose of the compounds administered to a human or other animal range from about 0.01 mg/kg body weight to about 100 mg/kg body weight of a mammal, for example, in the range of from about 0.03 mg/kg body weight to about 30 mg/kg body weight. If desired, the effective daily dose can be divided into multiple doses for purposes of administration. Consequently, single dose compositions can contain such amounts or submultiples thereof to make up the daily dose. It is understood that the effective daily dose can vary with the duration of the treatment.

d. PHARMACEUTICAL COMPOSITIONS

Further provided herein are pharmaceutical compositions that comprise one or more compounds described herein, or pharmaceutically acceptable salts, solvates, or salts of solvates thereof, formulated together with one or more pharmaceutically acceptable carriers.

Another aspect provides pharmaceutical compositions comprising one or more compounds described herein, or pharmaceutically acceptable salts, solvates, or salts of solvates thereof, and one or more pharmaceutically acceptable carriers, alone or in combination with one or more analgesics (e.g. acetaminophen), or in combination with one or more nonsteroidal anti-inflammatory drugs (NSAIDs), or a combination thereof, formulated together with one or more pharmaceutically acceptable carriers.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, excipient, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds' can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound can be mixed under sterile conditions with a pharmaceutically acceptable carrier and any needed preservatives, buffers or propellants which can be required. Opthalmic formulations, eye ointments, powders and solutions are also contemplated as being within the scope of this invention.

e. SALTS

The phrase "pharmaceutically acceptable salts" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in (J. Pharmaceutical Sciences, 1977, 66: 1 et seq). When the compound described herein is acidic, its corresponding salt can be prepared in situ during the final isolation and purification of the compounds by reacting a carboxylic acid-containing moiety with pharmaceutically acceptable non-toxic bases, including inorganic bases and organic bases. Salts derived from such inorganic bases include lithium, sodium, potassium, calcium, magnesium, ammonium, copper (II), copper (I), ferrous, ferric, manganese, zinc, tetramethylammonium, tetraethylammonium, and aluminum. Preferred are the ammonium, calcium, magnesium, potassium, and sodium salts. Salts derived from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethanolamine, diethylamine, 2-diethylaminoethanol, dimethylamine, 2-dimethylaminoethanol, ethanolamine, ethylamine, ethylenediamine, N-ethyl-morpholine, N-ethylpiperidine, glucamine, glucosamine, histidine, hydrabamine, isopropylamine, dicyclohexylamine, lysine, methylamine, methylglucamine, morpholine, piperazine, piperidine, polyamine resins, procaine, purines, theobromine, triethylamine, trimethylamine, tripropylamine, tromethamine, and the like.

When the compound is basic, its corresponding salt can be prepared from pharmaceutically acceptable non-toxic inorganic or organic acids. Such acid Such acid salts include, for example, acetate, adipate, alginate, citrate, aspartate, benzoate, benzenesulfonate, bisulfate, butyrate, camphorate, camphorsulfonate, digluconate, ethanesulfonate, gluconate, glycerophosphate, hemisulfate, heptanoate, hexanoate, fumarate, hydrochloride, hydrobromide, hydroiodide, 2-hydroxyethanesulfonate (isothionate), lactate, malate, maleate, mandelate, methanesulfonate, nitrate, nicotinate, 2-naphthalenesulfonate, oxalate, palmitate, pamoate, pectinate, persulfate, 3-phenylpropionate, picrate, pivalate, propionate, succinate, sulfate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Preferred are citrate, bromide, chloride, maleate, phosphate, sulfate, and tartrate.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. SOLUBILITY PROFILE

This prodrug approach enhances the water solubility of Example 18 as measured using the methods described below and reported in Table 1. The improvements offered by the prodrugs are beneficial, for they facilitate formulation and administration of the drug.

Approximately 3 mg of prodrug was weighed into a vial and 750 μL of water or 0.1 N aqueous HCl was added. The mixtures were vortexed to wet the solids. The mixtures were equilibrated for 1 hour with gentle agitation in a constant temperature water bath (T=25° C. for water samples and T=37° C. for 0.1 N HCl samples). After equilibration, the mixtures were visually inspected to assure that the amount of excess solid was sufficient to permit re-characterization. If not, solubility was reported as greater than the weighed concentration of prodrug (concentrations were confirmed by HPLC). The solid phase was then separated from the liquid phase by filtration through a 13 mm 0.45 μm GHP syringe filter (Pall Corporation). The filtrate was diluted as needed for quantification of the material studied by HPLC, and the concentration of the filtrate was reported as the solubility of the prodrug in the given medium.

TABLE 1

| Example | Media | Solubility (mg/mL) |
| --- | --- | --- |
| 18 | Water | <0.000020 |
| 18 | 0.1N HCl | 0.0043 |
| 1 | Water | 1.8 |
| 1 | 0.1N HCl | 2.5 |
| 2 | Water | 2.3 |
| 2 | 0.1N HCl | 4.1 |
| 3 | Water | 1.2 |
| 3 | 0.1N HCl | >4.1 |
| 4 | Water | 3.3 |
| 4 | 0.1N HCl | 0.2 |
| 5 | 0.1N HCl | 0.016 |
| 5 | Water | 0.74 |
| 6 | 0.1N HCl | >4.1 |
| 6 | Water | 2.3 |
| 7 | 0.1N HCl | >4.3 |
| 7 | Water | >4.3 |
| 8 | 0.1N HCl | >4.0 |
| 8 | Water | 3.9 |
| 9 | 0.1N HCl | 0.007 |
| 9 | Water | 0.83 |
| 14 | 0.1N HCl | 0.01 |
| 14 | Water | 0.073 |
| 15 | 0.1N HCl | >4.0 |
| 15 | Water | 0.68 | g. MEASUREMENT OF THE IN VIVO REGENERATION OF THE PARENT COMPOUND

Male Sprague-Dawley rats, weighing 250-400 g, were obtained from Charles Rivers Laboratories. For the initial screening, each prodrug was evaluated in one group of three rats. All rats received an oral aqueous formulation (suspension or solution), administered by gavage. Sequential blood samples were obtained from a tail vein of each animal for 24 hours after dosing. Plasma was separated by centrifugation and stored frozen until analysis. Compounds were selectively removed from the plasma using protein precipitation followed by reverse phase HPLC with MS/MS detection for quantitation. Attempts were made to measure both the prodrug and the parent compounds in each sample. Measurable levels of parent (Example 18) but not prodrug were detected after dosing Examples 1-11, 13, 14, 16, and 17. Measurable concentrations of both parent (Example 18) and prodrug were detected after dosing Examples 12 and 15.

h. GENERAL SYNTHESIS

The compounds can be prepared by a variety of processes well known for the preparation of compounds of this class. For example, the compounds described herein wherein the groups $R^{1a}$, $R^{1b}$, $R^{1c}$, $R^{1d}$, $R^{qe}$, $R^{qf}$, $R^p$, $R^y$, v, $R^x$, u, q2, $R^{aa}$, $R^{ab}$, $R^{ac}$, $R^{ad}$, $R^{1e}$, $R^{1f}$, q4, $A^2$, $L^2$, $R^{2A}$, $R^{3A}$, $R^{4A}$, q1, $X_1$-$X_4$, and z have the meanings as set forth in the summary section unless otherwise noted, can be synthesized as shown in Schemes 1-16.

Abbreviations which have been used in the descriptions of the Schemes and the Examples that follow are: DMAP for 4-(dimethylamino)pyridine, DMF for N,N-dimethylformamide, DMSO for dimethyl sulfoxide, EtOAc for ethyl acetate, HATU for O-(7-azabenzotriazol-1-yl)-N,N,N',N'-tetramethyluronium hexafluorophosphate, MeOH for methanol, and THF for tetrahydrofuran.

Compounds disclosed herein can be prepared as depicted in the following schemes:

Scheme 1

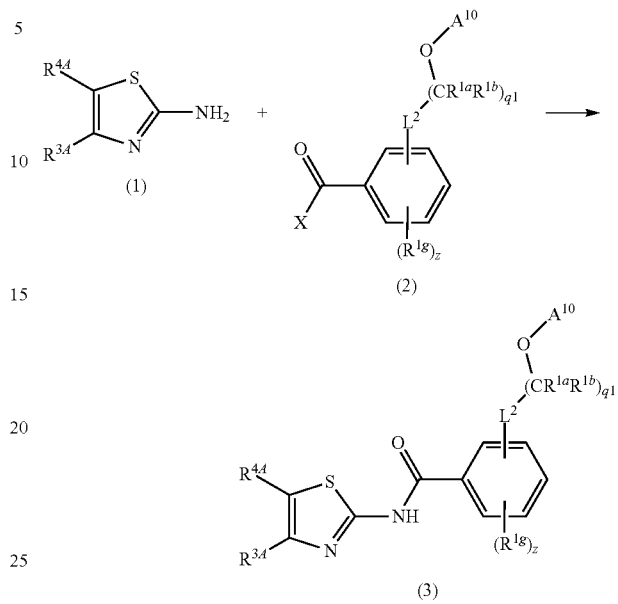

As shown in Scheme 1, compounds of formula (1) containing an amine group when treated with compounds of formula (2), wherein X is chloro or —OH and $A^{10}$ is hydrogen or a suitable hydroxy-protecting group, under coupling conditions known to one skilled in the art, provide compounds of formula (3). Typical conditions for the reaction of compounds of formula (2) wherein X is chloro and compounds of formula (1) include but are not limited to stirring an about equimolar mixture of the compounds in a solvent such as, but not limited to, chloroform, dichloromethane, THF, or mixture thereof, in the presence of a base such as, but not limited to, diisopropylethylamine, at a temperature ranging from about 0° C. to about 30° C. for about 8-24 hours. Acid coupling conditions of compounds of formula (2) wherein X is —OH and compounds of formula (1), include stirring an about equimolar mixture of the compounds in a solvent such as, but not limited to, THF, N,N-dimethylacetamide, N,N-dimethylformamide, pyridine, chloroform, or mixture thereof, with a coupling reagent, optionally along with a coupling auxiliary, and in the presence or absence of a base. Typical reactions can be carried out at temperature ranging from about 0° C. to about 65° C. or can be carried out in a microwave reactor to facilitate the coupling. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 1-propanephosphonic acid cyclic anhydride. Non-limiting examples of coupling auxiliary include 1-hydroxy-7-azabenzotriazole (HOAT) and 1-hydroxybenzotriazole hydrate (HOBT). Suitable examples of bases include, but are not limited to, N-methyl morpholine and diisopropylethylamine.

Certain compounds of formula (1) are available from commercial sources or can be prepared according to the methods described in the following references: Phosphorus, Sulfur and Silicon and the Related Elements, 181(7), 1665-1673 (2006); Revista de Chimie, 56(6), 659-662 (2005); Actes du Colloque Franco-Roumain de Chimie Appliquee, 3rd, Bacau, Romania, September 22-26, 117-120 (2004); Revista de Chimie, 55 (11), 889-893 (2004); Ger. Offen. 3533331; Monatshefte Fuer Chemie, 119(3), 333-9 (1988); Heterocycles, 26(3), 689-97 (1987).

For groups $A^{10}$ that contain a protecting group, such groups can be removed using chemical techniques that are well- Scheme 2

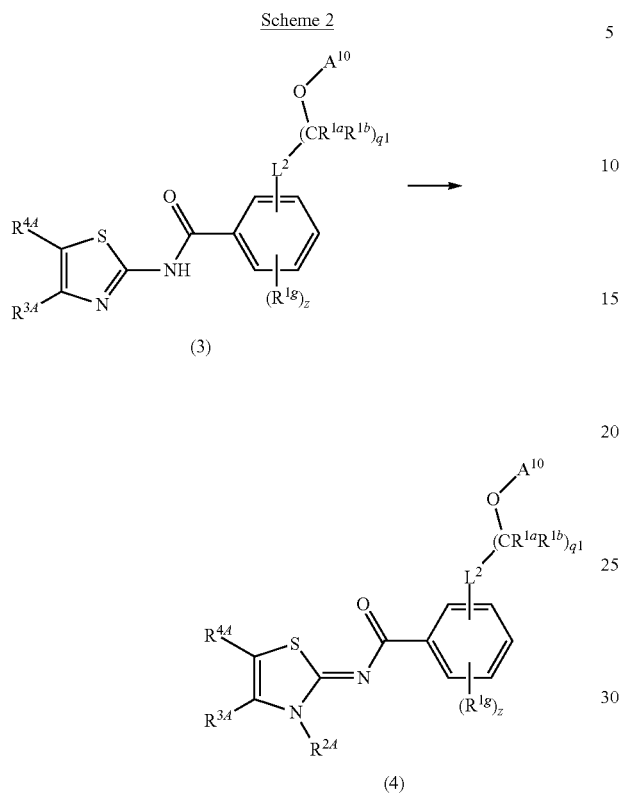

As shown in Scheme 2, compounds of formula (3), wherein $A^{10}$ is hydrogen or a suitable hydroxy-protecting group can be converted to compounds of general formula (4). Typical conditions include, but are not limited to, the treatment of compounds of formula (3) with sodium hydride in DMF at a temperature ranging from about 0° C. to about ambient temperature, followed by the addition of reagents such as $R^{2A}$—Y wherein Y is chloro, bromo, iodo, mesylate or triflate. Alternatively, reaction of (3) with other bases such as potassium hydroxide or potassium tert-butoxide in a mixture of THF and DMF, followed by treatment with $R^{2A}$—Y can also provide compounds of formula (4). Compounds (3) can also be converted to compounds of formula (4) using phase transfer conditions, for example, by refluxing compound (3) with compounds of formula $R^{2A}$—Y in toluene in the presence of a base like potassium carbonate and a phase transfer agent such as, but not limited to, tetrabutylammonium iodide, tetrabutylammonium hydrogensulfate, tetraethylammonium iodide and the like.

Scheme 3

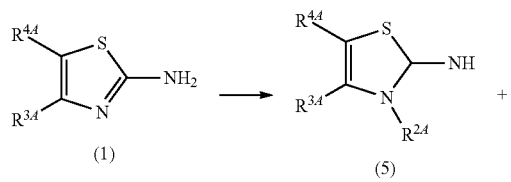

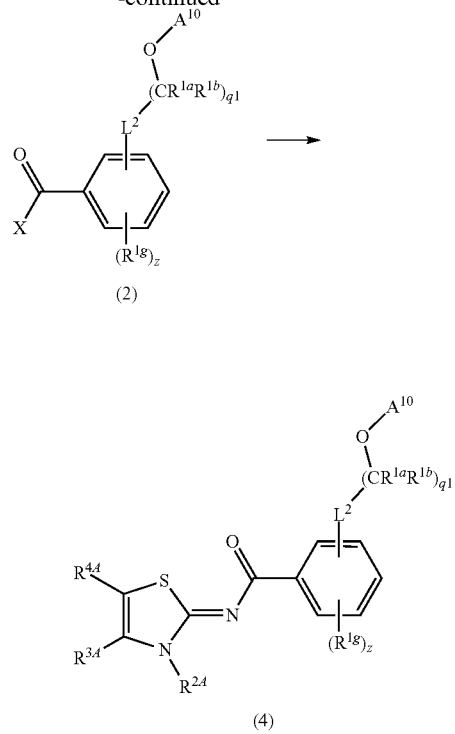

Alternatively, compounds of general formula (4) can also be prepared according to the methods outlined in Scheme 3. Compounds of formula (1) when treated with sodium hydride in DMF at about 0° C., followed by the addition of reagents such as $R^{2A}$—Y wherein and Y is chloro, bromo, iodo, tosylate, mesylate, or triflate provide compounds of formula (5). Alternatively, compounds of formula (1) can be heated neat or in the presence of a minimal amount of solvent to facilitate mixing, with compounds of formula $R^{2A}$—Y to obtain compounds of formula (5). Compounds of formula (5) can be isolated as a salt or a free base. The treatment of compounds of formula (5) with compounds of formula (2), wherein X is chloro or —OH, under coupling conditions as outlined in Scheme 1 generates compounds of formula (4).

Scheme 4

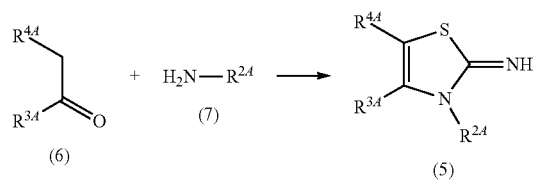

Compounds of formula (5) can be prepared according to the sequence outlined in Scheme 4. Carbonyl compounds (6) can be reacted at about room temperature with amino compounds (7) in a solvent such as, but not limited to, acetonitrile, tetrahydrofuran, methylene chloride, or mixture thereof, for about 1-24 hours in the presence of a dehydrating agent such as, but not limited to, 4 Å molecular sieves, followed by the addition of potassium thiocyanate and iodine with heating at about 50° C. for about 4-24 hours to provide the compounds (5).

Scheme 5

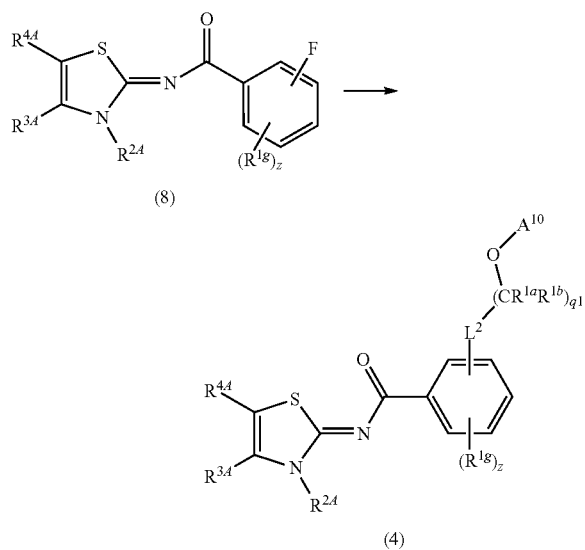

Compounds of formula (8) can be prepared according to the methods illustrated in Schemes 1-4, and 6. Compounds of formula (4) can be prepared from compounds of formula (8) by reaction with an appropriate alcohol or amine of formula $HL^2(CR^{1a}R^{1b})_{q1}$-$A^{10}$ wherein $L^2$ is O, N(H), or N(alkyl); and $A^{10}$ is hydrogen or a suitable hydroxy-protecting group, with a base such as, but not limited to, sodium tert-butoxide, potassium tert-butoxide or sodium hydride in a solvent such as, but not limited to, tetrahydrofuran or N,N-dimethylformamide.

Scheme 6

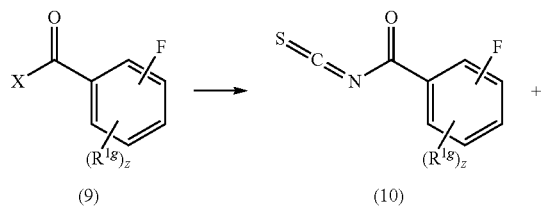

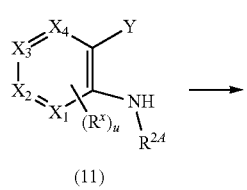

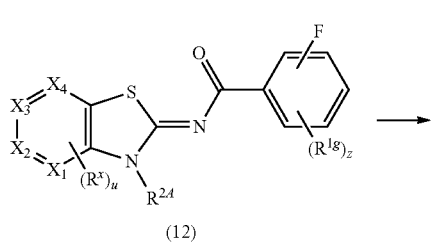

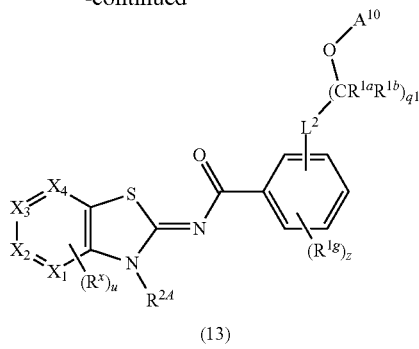

Compounds of formula (13) wherein $A^{10}$ is as defined above and one of $X_1$-$X_4$ is N and the others are CH can be prepared according to the sequence outlined in Scheme 6. Compounds of formula (9) wherein X is chloro or —OH under coupling conditions known to one skilled in the art can be treated with potassium thiocyanate to provide compounds of formula (10). Compounds of formula (10) wherein Y is Cl, Br, or I can be treated with compounds of formula (11) (prepared, for example, by alkylation or reductive amination of commercially available heteroaryl amines under conditions known to one skilled in the art) to provide compounds of formula (12). Utilizing reaction conditions as described in Scheme 5, compounds of formula (13) can be prepared from compounds of formula (12).

Scheme 7

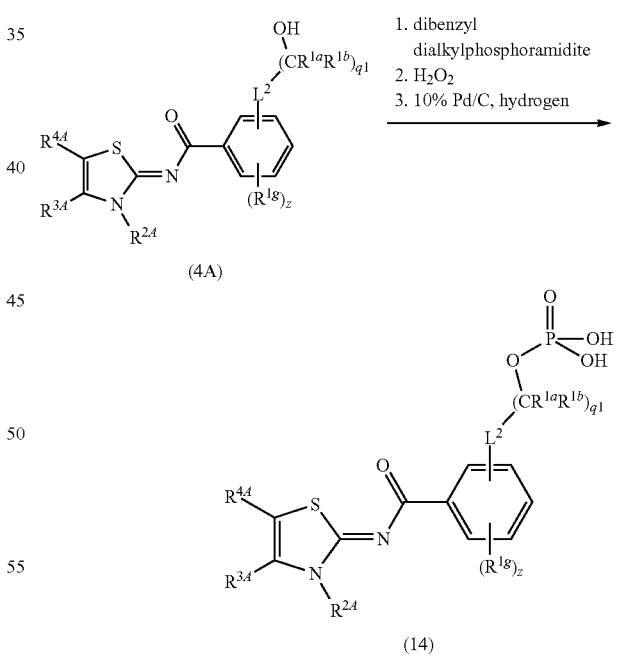

As shown in Scheme 7, compounds of formula (4A) (prepared from the removal of the hydroxy-protecting group of compounds (4) using chemical techniques that are well-known to those skilled in the art; examples of which can be found in T. Greene and P. Wuts, Protecting Groups in Chemical Synthesis (3$^{rd}$ ed.), John Wiley & Sons, NY (1999)) can be converted to compounds of general formula (14). Typical conditions include, but are not limited to, the treatment of compounds of formula (4) with dibenzyl diisopropylphosphoramidite and tetrazole in THF at a temperature ranging from about 0° C. to about ambient temperature. After stirring for about 4-20 hours, an oxidant such as t-butyl hydroperoxide or m-chloro perbenzoic acid (m-CPBA) is added to form the bisbenzyl phosphate. Formation of the desired phosphate of formula (14) is accomplished by hydrogenolysis of the benzyl ethers under standard conditions.

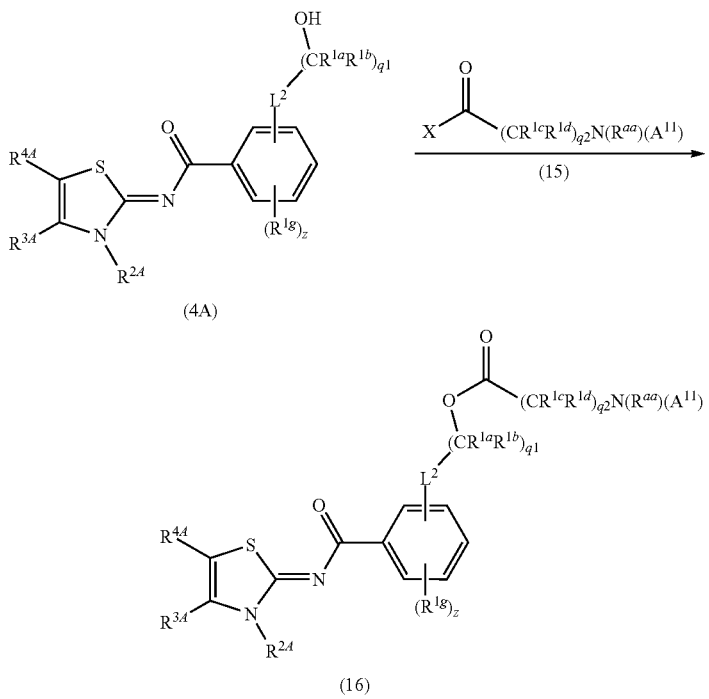

As shown in Scheme 8, compounds of formula (4A) when treated with compounds of formula (15), wherein X is chloro or —OH, under coupling conditions as outlined in Scheme 1 generate compounds of formula (16). In compounds of formula (15), $A^{11}$ is a suitable nitrogen protecting group or $R^{ab}$. For groups $A^{11}$ that contain a nitrogen protecting group, such groups can be removed using chemical techniques that are well-known to those skilled in the art; examples of which can be found in T. Greene and P. Wuts, Protecting Groups in Chemical Synthesis ($3^{rd}$ ed.), John Wiley & Sons, NY (1999). Following removal of any protecting group, molecules can be further transformed to compounds of the invention using standard chemical techniques well-known to those skilled in the art such as alkylation, reductive amination and the like.

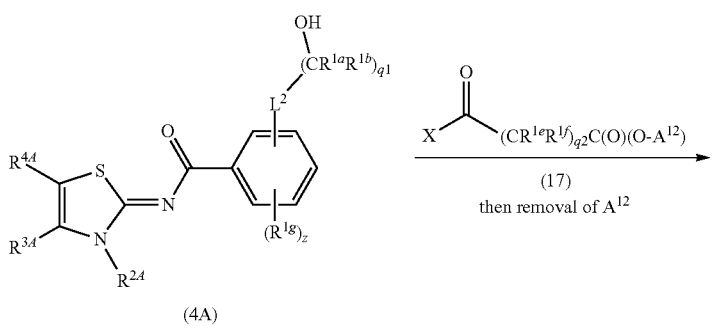

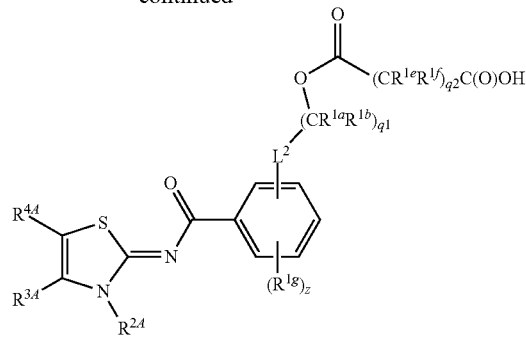

(18)

As shown in Scheme 9, compounds of formula (4A) when treated with compounds of formula (17), wherein X is chloro or —OH, under coupling conditions as outlined in Scheme 1 provide compounds of formula (18). In compounds of formula (17), $A^{12}$ is a group that can be easily removed after coupling to provide carboxylic acid derivatives of formula (18). Examples of such groups are tert-butyl, which can be removed by treatment with HCl, or $A^{12}$ is a benzyl group which can be removed under standard hydrogenolysis conditions.

Scheme 10

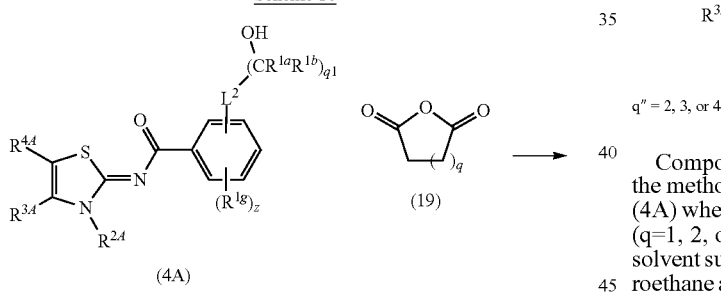

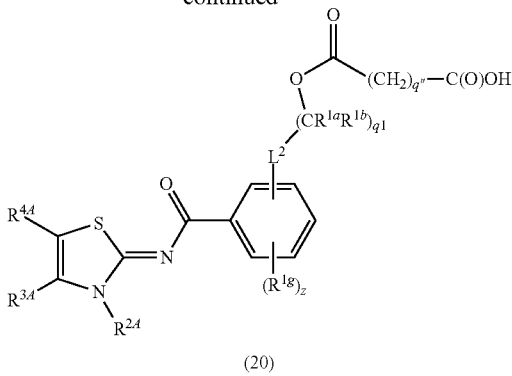

(20)

$q'' = 2, 3,$ or $4$

Compounds of formula (20) can be prepared according to the method illustrated in Scheme 10. Compounds of formula (4A) when treated with succinic, glutaric or adipic anhydride (q=1, 2, or 3, respectively) and dimethylaminopyridine in a solvent such as, but not limited to, dichloromethane or dichloroethane and stirred at temperatures ranging from about room temperature to about 80° C. provide compounds of formula 20, wherein q'' is 2, 3, or 4.

Scheme 11

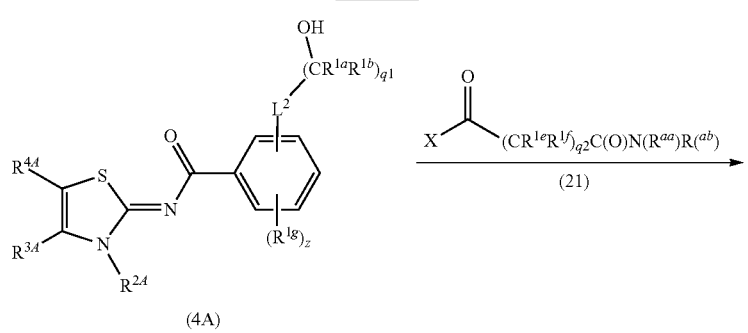

-continued

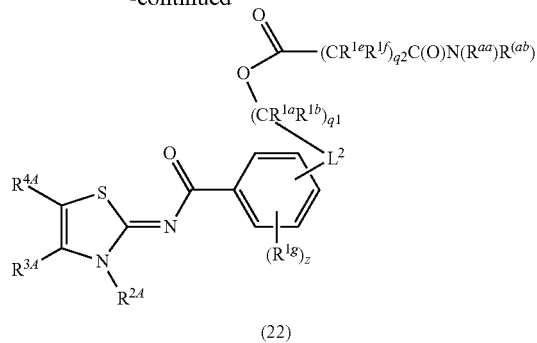

(22)

As shown in Scheme 11, compounds of formula (4A) when treated with compounds of formula (21), wherein X is chloro or —OH, under coupling conditions as outlined in Scheme 1 provide compounds of formula (22).

imidazol-1-yl)methanone and a tertiary amine base such as triethylamine in a solvent such as THF. The resulting active esters of formula (4) can be treated with a variety of suitable aminoalcohol derivatives to provide compounds of formula (23).

Scheme 12

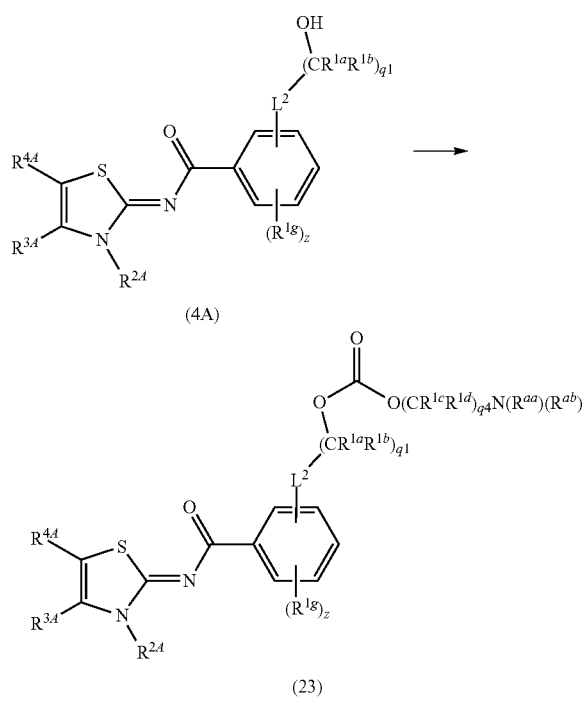

Scheme 13

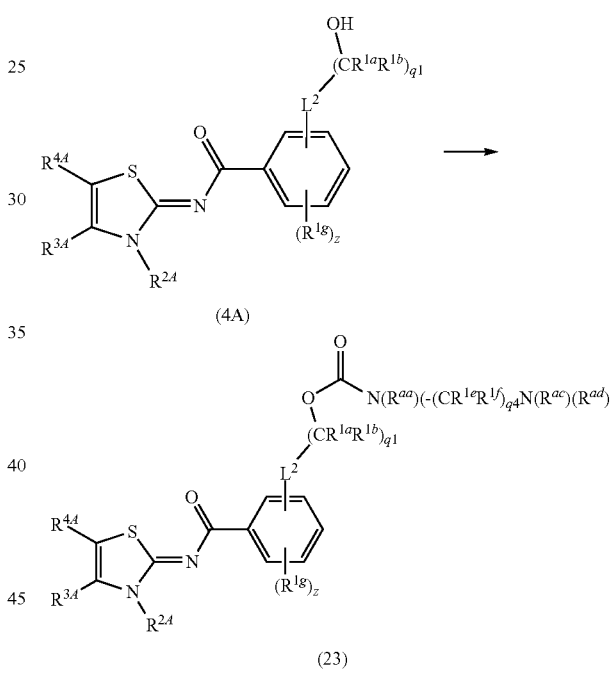

As shown in Scheme 12, compounds of formula (4A) can be transformed into active ester derivatives by treatment with an agent such as but not limited to triphosgene, 4-nitrophenyl carbonochloridate, bis(4-nitrophenyl)carbonate or di(1H-

As illustrated in Scheme 13, compounds of formula (23) can be generated by addition appropriately substituted diamines to active ester derivates of compound (4A), which can be prepared as outlined in Scheme 12.

Scheme 14

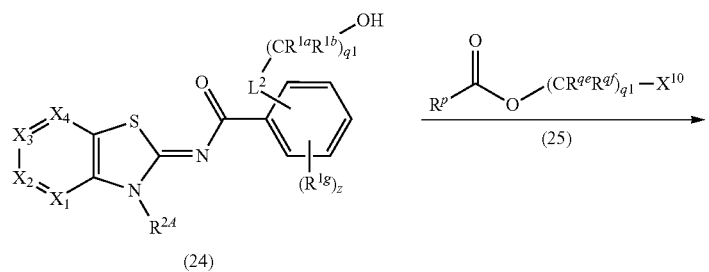

(24)

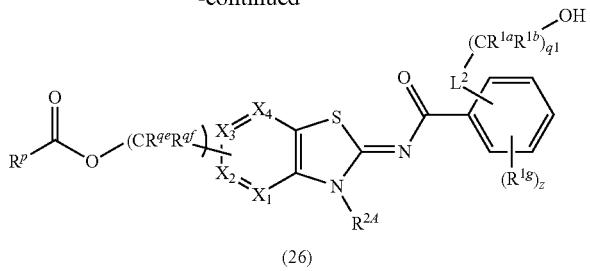

(26)

Compounds of formula (24), wherein one of $X_1$, $X_2$, $X_3$ and $X_4$ is nitrogen can be prepared as described in Schemes 1-6. Compounds of formula (25) wherein $X^{10}$ is typically chloro or bromo, are commercially available or can be prepared as described in Davidsen, S. K. et al. J. Med. Chem. 1994, 37, 4423-4429. As illustrated in Scheme 14, compounds of formula (24) in a solution such as acetonitrile can be treated with compounds of formula (25) and then warmed to reflux for about 2 to 14 hours to generate pyridinium prodrugs of formula (26).

Scheme 15

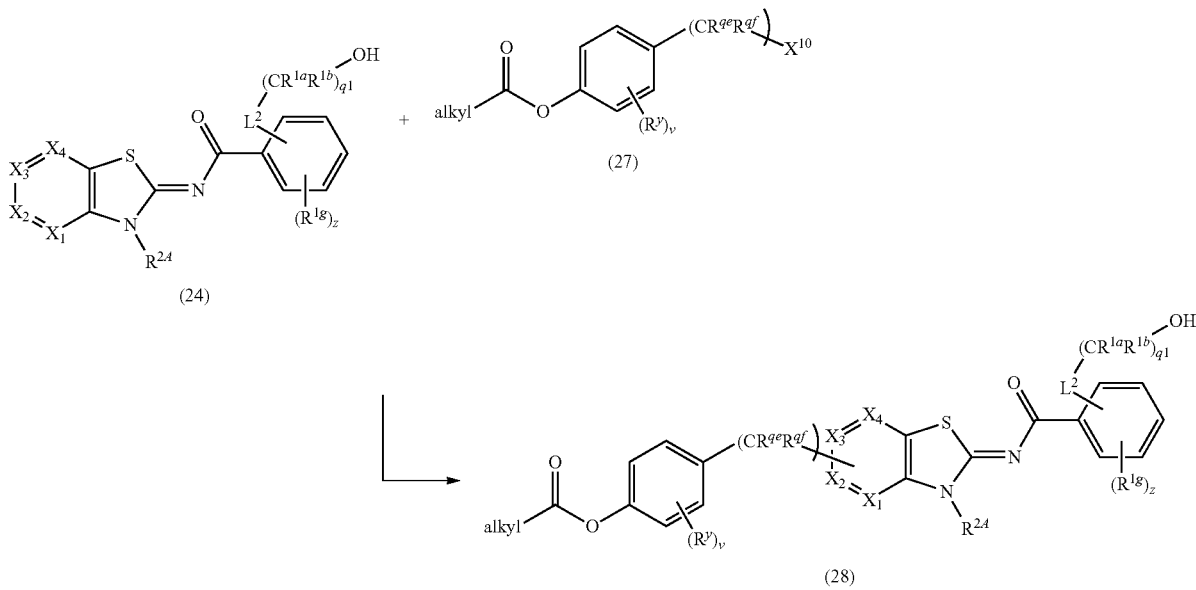

As illustrated in Scheme 15, compounds of formula (24), wherein one of $X_1$, $X_2$, $X_3$ and $X_4$ is nitrogen can be treated with compounds of formula (27) wherein $X^{10}$ is typically chloro or bromo, to generate pyridinium salts of formula (28).

Scheme 16

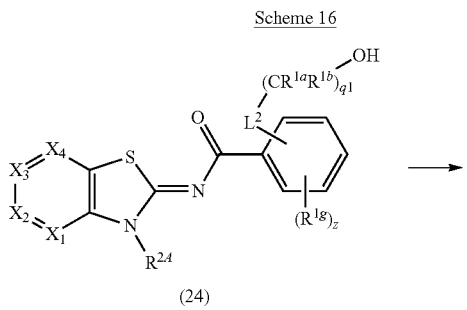

(24)

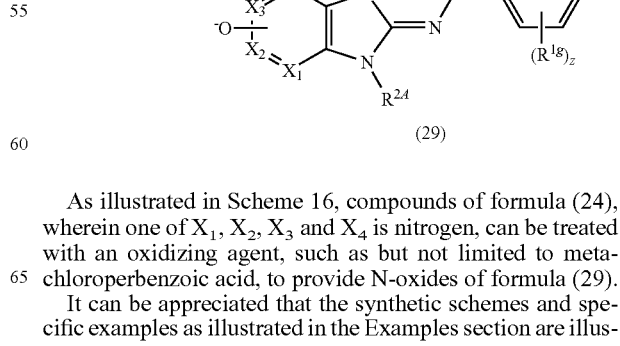

(29)

As illustrated in Scheme 16, compounds of formula (24), wherein one of $X_1$, $X_2$, $X_3$ and $X_4$ is nitrogen, can be treated with an oxidizing agent, such as but not limited to meta-chloroperbenzoic acid, to provide N-oxides of formula (29).

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, titration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; and can be found in T. Greene and P. Wuts, Protecting Groups in Chemical Synthesis (3$^{rd}$ ed.), John Wiley & Sons, NY (1999). Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

i. EXAMPLES

Example 1

(2Z)-5-[(acetyloxy)methyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium bromide To a solution of Example 18C (340 mg, 0.750 mmol) in acetonitrile (7.50 mL) was added neat bromomethyl acetate (Aldrich, 220 mg, 1.50 mmol). The white slurry was refluxed overnight during which time a precipitate gradually formed. After cooling to ambient temperature, the volatiles were removed by rotary evaporator. Purification by chromatography (silica gel, 10-50% methanol in dichloromethane) afforded 232 mg (51%) of the title compound that was recrystallized from acetonitrile. $^1$H NMR (DMSO-d$_6$) δ 0.98 (t, J=7.5 Hz, 3H), 1.23 (d, J=5.8 Hz, 3H), 1.39-1.51 (m, 2H), 1.80-1.90 (m, 2H), 2.17 (s, 3H), 3.97-4.10 (m, 3H), 4.52 (t, J=7.1 Hz, 2H), 4.85 (d, J=4.4 Hz, 1H), 6.47 (s, 2H), 7.41 (d, J=8.8 Hz, 1H), 7.91 (dd, J=8.6, 2.2 Hz, 1H), 8.38 (d, J=20 Hz, 1H), 8.73 (d, J=6.4 Hz, 1H), 9.00 (dd, J=6.4, 1.0 Hz, 1H), 9.69 (br s, 1H). LC-MS (ESI+) m/z 526 (M)$^+$.

Example 2

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-methylalaninate Example 2A (1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl N-(tert-butoxycarbonyl)-2-methylalaninate To a solution of Example 18C (453 mg, 1.00 mmol), 2-(tert-butoxycarbonylamino)-2-methylpropanoic acid (Aldrich, 508 mg, 2.50 mmol), O-(7-azabenzotriazol-1-yl)-N,N,N',N'-tetramethyluronium hexafluorophosphate (HATU) (Aldrich, 948 mg, 2.50 mmol), and dimethylaminopyridine (Aldrich, 30.5 mg, 0.250 mmol) in anhydrous N,N-dimethylformamide (6 mL) was added triethylamine (Aldrich, 0.697 mL, 5.00 mmol). The mixture was stirred at 50° C. overnight. The volatiles were removed by rotary evaporator. Purification by chromatography (silica gel: 20-70% ethyl acetate in hexanes) afforded 329 mg (51%) of the title compound as a white solid. MS (ESI$^+$) m/z 639 (M+H)$^+$.

Example 2B (1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-methylalaninate To a solution of Example 2A (265 mg, 0.415 mmol) in anhydrous dichloromethane (4 mL) was added trifluoroacetic acid (Aldrich, 0.320 mL, 4.15 mmol). The solution was stirred at room temperature overnight, then saturated sodium bicarbonate solution was added to adjust the pH to 9. The mixture was extracted with dichloromethane (3×15 mL). The combined organic extracts were dried over sodium sulfate, filtered, and concentrated by rotary evaporator. Purification by flash chromatography (silica gel: 50-100% ethyl acetate in hexanes) afforded 202 mg (90%) of the title compound. $^1$H NMR (DMSO-d$_6$) δ 0.94 (t, J=7.3 Hz, 3H), 1.08 (s, 3H), 1.10 (s, 3H), 1.30 (d, J=6.8 Hz, 3H), 1.34-1.46 (m, 3H), 1.77-1.87 (m, 3H), 4.19-4.32 (m, 2H), 4.53 (t, J=7.3 Hz, 2H), 5.08-5.18 (m, 1H), 7.39 (d, J=8.8 Hz, 1H), 7.84 (dd, J=8.6, 2.2 Hz, 1H), 8.03 (d, J=4.4 Hz, 1H), 8.23 (d, J=2.0 Hz, 1H), 8.50 (d, J=5.1 Hz, 1H), 9.03 (s, 1H). MS (ESI+) m/z 539 (M+H)$^+$.

To a solution of the free base above in dichloromethane (5 mL) was added a 1.0 M solution of etheric hydrogen chloride (Aldrich, 4.15 mL, 4.15 mmol) to form a white slurry. The mixture was stirred at room temperature for 2 hours. The volatiles were removed by rotary evaporator. Titration with acetonitrile afforded 158 mg of the hydrogen chloride salt of the title compound as a white solid. LC-MS (ESI+) m/z 539 (M+H)$^+$.

Example 3

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl glycinate Example 18C and N-(t-butoxycarbonyl)glycine (Aldrich) were processed as described in Examples 2A and 2B to afford the title compound. ¹H NMR (DMSO-d₆) δ 0.95 (t, J=7.5 Hz, 3H), 1.33 (d, J=6.4 Hz, 3H), 1.35-1.47 (m, 2H), 1.65 (br s, 2H), 1.78-1.88 (m, 2H), 3.23 (s, 2H), 4.17-4.31 (m, 2H), 4.54 (t, J=7.3 Hz, 2H), 5.17-5.27 (m, 1H), 7.37 (d, J=8.5 Hz, 1H), 7.85 (dd, J=9.0, 2.2 Hz, 1H), 8.02 (dd, J=5.1, 0.7 Hz, 1H), 8.27 (d, J=2.0 Hz, 1H), 8.50 (d, J=5.1 Hz, 1H), 9.04 (s, 1H). MS (ESI+) m/z 511 (M+H)⁺.

The hydrogen chloride salt was prepared according to the method described for Example 2B. MS (ESI+) m/z 511 (M+H)⁺.

Example 4

(2Z)-3-butyl-5-{[(2,2-dimethylpropanoyl)oxy]methyl}-2-{[2-{[(2S)-2-hydroxypropyl]oxy}-5-(trifluoromethyl)benzoyl]imino}-2,3-dihydro[1,3]thiazolo[4,5-c]pyridin-5-ium chloride Example 18C and chloromethyl pivalate (Aldrich) were processed as described in Example 1 to afford the title compound. ¹H NMR (DMSO-d₆) δ 0.96 (t, J=7.3 Hz, 3H), 1.20 (s, 9H), 1.23 (d, J=6.0 Hz, 3H), 1.38-1.51 (m, 2H), 1.79-1.89 (m, 2H), 3.96-4.12 (m, 3H), 4.53 (t, J=7.3 Hz, 2H), 4.89 (d, J=4.4 Hz, 1H), 6.52 (s, 2H), 7.42 (d, J=8.7 Hz, 1H), 7.91 (dd, J=8.9, 2.2 Hz, 1H), 8.37 (d, J=2.4 Hz, 1H), 8.76 (d, J=6.3 Hz, 1H), 9.03 (d, J=6.7 Hz, 1H), 9.82 (s, 1H). MS (ESI+) m/z 568 (M)⁺.

Example 5

(2Z)-5-[(benzoyloxy)methyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium chloride Example 18C and chloromethyl benzoate (prepared as described in Davidsen, S. K. et al J. Med. Chem. 1994, 37, 4423-4429) were processed as described in Example 1 to afford the title compound. ¹H NMR (DMSO-d₆) δ 0.96 (t, J=7.3 Hz, 3H), 1.22 (d, J=6.0 Hz, 3H), 1.39-1.51 (m, 2H), 1.81-1.91 (m, 2H), 3.96-4.11 (m, 3H), 4.54 (t, J=7.3 Hz, 2H), 4.87 (d, J=4.0 Hz, 1H), 6.76 (s, 2H), 7.41 (d, J=8.7 Hz, 1H), 7.56-7.61 (m, 2H), 7.72-7.78 (m, 1H), 7.91 (dd, J=8.9, 2.6 Hz, 1H), 8.04-8.07 (m, 2H), 8.38 (d, J=2.4 Hz, 1H), 8.76 (d, J=6.3 Hz, 1H), 9.15 (d, J=6.3 Hz, 1H), 9.86 (s, 1H). MS (ESI+) m/z 588 (M)⁺.

Example 6

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl L-alaninate Example 18C and N-(t-butoxycarbonyl)-L-alanine (Alfa) were processed as described in Examples 2A and 2B to afford the title compound. ¹H NMR (DMSO-d₆) δ 0.94 (t, J=7.3 Hz, 3H), 1.04 (d, J=7.1 Hz, 3H), 1.32 (d, J=6.4 Hz, 3H), 1.34-1.47 (m, 2H), 1.67 (br s, 2H), 1.77-1.87 (m, 2H), 3.38-3.45 (m, 1H), 4.17-4.32 (m, 2H), 4.50-4.56 (m, 2H), 5.12-5.22 (m, 1H), 7.38 (d, J=8.8 Hz, 1H), 7.85 (dd, J=8.8, 2.0 Hz, 1H), 8.03 (d, J=5.1 Hz, 1H), 8.24 (d, J=2.4 Hz, 1H), 8.50 (d, J=5.4 Hz, 1H), 9.03 (s, 1H). MS (ESI+) m/z 525 (M+H)⁺.

The hydrogen chloride salt was prepared according to the method described for Example 2B. MS (ESI+) m/z 525 (M+H)⁺.

Example 7

(2Z)-3-butyl-2-{[2-{[(2S)-2-hydroxypropyl]oxy}-5-(trifluoromethyl)benzoyl]imino}-5-[({[(2S)-2-(methoxycarbonyl)pyrrolidin-1-yl]carbonyl}oxy)methyl]-2,3-dihydro[1,3]thiazolo[4,5-c]pyridin-5-ium chloride Example 18C and N-([chloromethyl]oxy)carbonyl-L-proline methyl ester (prepared according to the method described in Davidsen, S. K. et al J. Med. Chem. 1994, 37, 4423-4429) were processed as described in Example 1 to afford the title compound. ¹H NMR (DMSO-d₆) δ 0.94-1.00 (m, 3H), 1.15-1.28 (m, 3H), 1.39-1.51 (m, 2H), 1.70-2.01 (m, 5H), 2.14-2.33 (m, 1H), 3.37-3.42 (m, 1H), 3.51-3.55 (m, 1H), 3.63-3.67 (m, 3H), 3.96-4.10 (m, 3H), 4.26-4.56 (m, 3H), 4.88-4.90 (m, 1H), 6.41-6.57 (m, 2H), 7.40-7.43 (m, 1H), 7.89-7.93 (m, 1H), 8.38 (s, 1H), 8.74-8.76 (m, 1H), 8.94-9.03 (m, 1H), 9.70-9.80 (m, 1H). MS (ESI+) m/z 639 (M)⁺.

Example 8

(2Z)-3-butyl-5-({[(dimethylamino)carbonyl]oxy}methyl)-2-{[2-{[(2S)-2-hydroxypropyl]oxy}-5-(trifluoromethyl)benzoyl]imino}-2,3-dihydro[1,3]thiazolo[4,5-c]pyridin-5-ium chloride Example 18C and chloromethyl dimethylcarbamate (prepared according to the method described in Davidsen, S. K. et al J. Med. Chem. 1994, 37, 4423-4429) were processed as described in Example 1 to afford the title compound. ¹H NMR (DMSO-d₆) δ 0.97 (t, J=7.3 Hz, 3H), 1.22 (d, J=5.5 Hz, 3H), 1.39-1.51 (m, 2H), 1.80-1.90 (m, 2H), 2.85 (s, 3H), 2.95 (s, 3H), 3.97-4.11 (m, 3H), 4.51-4.56 (m, 2H), 4.88 (d, J=4.4 Hz, 1H), 6.46 (s, 2H), 7.41 (d, J=8.7 Hz, 1H), 7.91 (dd, J=8.9, 2.2 Hz, 1H), 8.38 (d, J=2.0 Hz, 1H), 8.73 (d, J=6.3 Hz, 1H), 9.02 (d, J=6.7 Hz, 1H), 9.76 (s, 1H). MS (ESI+) m/z 555 (M)⁺.

Example 9

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl dihydrogen phosphate Example 9A dibenzyl (1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl phosphate To a solution of Example 18C (907 mg, 2.00 mmol) and dibenzyl diisopropylphosphoramidite (Aldrich, 1.46 mL, 1.54 g, 4.00 mmol) in anhydrous tetrandyrofuran (20 mL) was added a solution of tetrazole (8.89 mL of 0.45 M solution in acetonitriole, 4.00 mmol) and the mixture was stirred at room temperature overnight. A solution of t-butyl hydroperoxide (0.364 mL of 5.5 M solution in decane, 2.00 mmol) was added and the resulting mixture stirred at room temperature for 4 hours. Water (25 mL) added and the mixture was extracted with dichloromethane (3×30 mL). The combined organic extracts were dried over sodium sulfate, filtered, and concentrated by rotary evaporator. Purification by flash chromatography (silica gel: 10-75% ethyl acetate in hexanes) afforded 1.30 g (91%) of the title compound. ¹H NMR (DMSO-d₆) δ 0.91 (t, J=7.3 Hz, 3H), 1.31-1.38 (m, 2H), 1.42 (d, J=6.4 Hz, 3H), 1.71-1.81 (m, 2H), 4.21-4.32 (m, 2H), 4.43-4.47 (m, 2H), 4.77-4.85 (m, 1H), 4.95-4.99 (m, 4H), 7.22 (br s, 5H), 7.29 (br s, 5H), 7.35 (d, J=8.8 Hz, 1H), 7.83 (dd, J=9.0, 2.2 Hz, 1H), 7.92 (dd, J=5.1 0.7 Hz, 1H), 8.25 (d, J=2.0 Hz, 1H), 8.48 (d, J=5.1 Hz, 1H), 8.97 (s, 1H). MS (ESI+) m/z 714 (M+H)⁺.

Example 9B (1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl dihydrogen phosphate A slurry of Example 9A (1.25 g, 1.75 mmol) and 10% palladium-on-carbon catalyst (Aldrich, 0.186 g) in ethyl acetate (20 mL) were stirred under an atmosphere of hydrogen gas (balloon) at room temperature overnight. After flushing the system with nitrogen gas, additional ethyl acetate (50 mL) was added. The mixture was heated to dissolve solids. While hot, the black catalyst was removed by vacuum filtration through a glass frit. The liquor was concentrated to give a white solid. The product was triturated with hot methanol to give 0.801 g (86%) of the title compound. $^1$H NMR (DMSO-$d_6$) δ 0.94 (t, J=7.5 Hz, 3H), 1.33-1.47 (m, 5H), 1.77-1.87 (m, 2H), 3.32 (br s, 2H), 4.14-4.27 (m, 2H), 4.51-4.61 (m, 3H), 7.36 (d, J=8.8 Hz, 1H), 7.84 (dd, J=8.8, 2.4 Hz, 1H), 8.01 (d, J=5.4 Hz, 1H), 8.31 (d, J=2.0 Hz, 1H), 8.50 (d, J=5.1 Hz, 1H), 9.03 (s, 1H). MS (ESI+) m/z 534 (M+H)$^+$.

Example 10

(2Z)-3-butyl-2-{[2-{[(2S)-2-hydroxypropyl]oxy}-5-(trifluoromethyl)benzoyl]imino}-5-[({[(3-methoxypropyl)amino]carbonyl}oxy)methyl]-2,3-dihydro[1,3]thiazolo[4,5-c]pyridin-5-ium chloride Example 18C and chloromethyl 3-methoxypropylcarbamate (prepared according to the method described in Davidsen, S. K. et al *J. Med. Chem.* 1994, 37, 4423-4429) were processed using as described in Example 1 to afford the title compound. $^1$H NMR (DMSO-$d_6$) δ 0.97 (t, J=7.3 Hz, 3H), 1.23 (d, J=5.8 Hz, 3H), 1.39-1.51 (m, 2H), 1.59-1.68 (m, 2H), 1.80-1.89 (m, 2H), 3.02-3.09 (s, 2H), 3.19 (s, 3H), 3.26-3.36 (m, 2H), 3.97-4.10 (m, 3H), 4.52 (t, J=7.3 Hz, 2H), 4.86 (d, J=4.4 Hz, 1H), 6.43 (s, 2H), 7.41 (d, J=8.8 Hz, 1H), 7.86-7.93 (m, 2H), 8.37 (d, J=2.0 Hz, 1H), 8.73 (d, J=6.4 Hz, 1H), 8.95 (d, J=6.8 Hz, 1H), 9.69 (s, 1H). MS (ESI+) m/z 599 (M)$^+$.

Example 11

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl N-methylglycinate Example 18C and 2-(tert-butoxycarbonyl(methyl)amino)acetic acid (Aldrich) were processed as described in Examples 2A and 2B to afford the title compound. $^1$H NMR (DMSO-$d_6$) δ 0.94 (t, J=7.3 Hz, 3H), 1.33 (d, J=6.4 Hz, 3H), 1.35-1.47 (m, 2H), 1.77-1.87 (m, 2H), 2.18 (s, 3H), 3.20-3.21 (m, 2H), 3.30 (br s, 1H), 4.18-4.32 (m, 2H), 4.53 (t, J=7.5 Hz, 2H), 5.19-5.29 (m, 1H), 7.38 (d, J=8.8 Hz, 1H), 7.85 (dd, J=8.8, 2.0 Hz, 1H), 8.02 (dd, J=5.4, 0.7 Hz, 1H), 8.26 (d, J=2.0 Hz, 1H), 8.50 (d, J=5.1 Hz, 1H), 9.04 (s, 1H). MS (ESI$^+$) m/z 525 (M+H)$^+$.

The hydrogen chloride salt was prepared according to the method described for Example 2B. MS (ESI$^+$) m/z 525 (M+H)$^+$.

Example 12

N-[(2Z)-3-butyl-5-oxido[1,3]thiazolo[4,5-c]pyridin-2(3H)-ylidene]-2-{[(2S)-2-hydroxypropyl]oxy}-5-(trifluoromethyl)benzamide Example 18C (100 mg, 0.221 mmol) in dichloromethane (5 mL) was treated with m-chloroperbenzoic acid (74.1 mg, 0.331 mmol) and the reaction mixture was stirred for 4 hours at room temperature. The mixture was diluted with dichloromethane and saturated aqueous NaHCO$_3$ and the layers separated. The organic extract was washed with brine, dried (MgSO$_4$) and concentrated. The residue was purified by flash chromatography (silica gel, 10% methanol in dichloromethane) to provide title compound. $^1$H NMR (300 MHz, CDCl$_3$) δ ppm 0.93-1.14 (m, 3H), 1.19-1.38 (m, 4H), 1.40-1.71 (m, 2H), 1.76-1.97 (m, 2H), 3.86 (t, J=8.8 Hz, 1H), 4.15-4.46 (m, 4H), 4.61 (s, 1H), 7.11 (d, J=8.8 Hz, 1H), 7.54 (d, J=6.1 Hz, 1H), 7.73 (dd, J=8.5, 2.4 Hz, 1H), 8.15 (d, J=6.1 Hz, 1H), 8.39 (s, 1H), 8.50 (d, J=2.4 Hz, 1H). MS (DCI/NH$_3$) m/z 470 (M+H)$^+$. Anal. Calculated for 0.5H$_2$O.C$_{21}$H$_{22}$F$_3$N$_3$O$_4$S: C, 52.71; H, 4.85; N, 8.78. Found: C, 52.68; H, 4.93; N, 8.43.

Example 13

(2Z)-5-[4-(acetyloxy)-3,5-dimethylbenzyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium bromide Example 13A 4-(bromomethyl)-2,6-dimethylphenyl acetate To a solution of commercially available 4-(hydroxymethyl)-2,6-dimethylphenyl acetate (1 g, 5.15 mmol) and perbromomethane (2.39 g, 7.21 mmol) in tetrahydrofuran (25 mL) was added triphenylphosphine (1.620 g, 6.18 mmol). The mixture was stirred at room temperature for 6 hours then concentrated under reduced pressure. The residue was purified by flash chromatography (silica gel, hexane:ethyl acetate 4:1) to provide the title compound (1.05 g, 80% yield). MS (DCI/NH$_3$) m/z 274 (M+NH$_4$)$^+$.

Example 13B (2Z)-5-[4-(acetyloxy)-3,5-dimethylbenzyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium bromide A mixture of Example 18C and Example 13A (64 mg, 0.249 mmol) in acetonitrile was stirred at room temperature for 18 hours. The reaction mixture was concentrated in vacuo and the residue was triturated with diethyl ether. The solid was filtered, washed with ether, and dried to provide the title compound. $^1$H NMR (300 MHz, CDCl$_3$) δ ppm 1.03 (t, J=7.3 Hz, 3H), 1.21-1.36 (m, 3H), 1.41-1.76 (m, 3H), 1.86-2.05 (m, 2H), 2.16 (s, 6H), 2.25-2.39 (m, 3H), 3.87 (t, J=8.5 Hz, 1H), 4.16-4.45 (m, 2H), 4.90 (t, J=7.5 Hz, 2H), 6.29 (s, 2H), 7.12 (d, J=8.8 Hz, 1H), 7.40 (s, 2H), 7.77 (dd, J=8.3, 2.2 Hz, 1H), 8.05 (d, J=6.4 Hz, 1H), 8.45 (d, J=6.8 Hz, 1H), 8.58 (d, J=2.4 Hz, 1H), 11.13 (s, 1H). Anal. Calculated for C$_{21}$H$_{22}$F$_3$N$_3$O$_4$S.HBr: C, 54.09; H, 4.96; N, 5.91. Found: C, 53.67; H, 4.96; N, 6.03.

Example 14

4-({(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl}oxy)-4-oxobutanoic acid To a solution of Example 18C (268 mg, 0.591 mmol), dimethylaminopyridine (0.072 g, 0.591 mmol) in dichloromethane (5 mL) was added succinic anhydride (0.296 g, 2.95 mmol), and the reaction mixture was stirred at 40° C. overnight. The mixture was concentrated, treated with 2 N HCl and extracted with EtOAc (3×10 mL). The organic extracts were combined, concentrated and dried to give a solid. To the solid was added saturated NaHCO$_3$ until basic, and then to 2 N HCl until acidic. The solid was filtered to afford title compound (230 mg, 70%). $^1$H NMR (300 MHz, DMSO-$d_6$) δ ppm 0.94 (t, J=7.34 Hz, 3H) 1.33 (t, J=5.95 Hz, 3H) 1.36-1.47 (m, 2H) 1.76-1.88 (m, 2H) 2.40-2.49 (m, 4H) 4.13-4.22 (m, 1H) 4.24-4.30 (m, 1H) 4.54 (t, J=7.34 Hz, 2H) 5.14-5.24 (m, 1H) 7.37 (d, J=8.72 Hz, 1H) 7.85 (dd, J=8.72, 2.38 Hz, 1H) 8.01 (d, J=5.16 Hz, 1H) 8.28 (d, J=2.38 Hz, 1H) 8.50 (d, J=5.16 Hz, 1H) 9.04 (s, 1H) 12.16 (s, 1H); MS (DCI/NH$_3$) m/z 554 (M+H)$^+$.

Example 15

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-(dimethylamino)ethylcarbamate To a solution of Example 18C (0.65 g, 1.43 mmol) and triethylamine (0.220 ml, 1.58 mmol) in THF (40 mL) at 0° C. was added triphosgene (0.140 g, 0.473 mmol) drop wise. After 30 minutes the mixture was filtered (EtOAc wash) and the filtrate was concentrated. To a 0° C. solution of the resultant residue (370 mg, 0.717 mmol) in dichloromethane (40 mL) was added a solution of N,N-dimethylethylene diamine (63.2 mg, 0.717 mmol) and triethylamine (0.150 mL, 1.076 mmol) in dichloromethane (5 mL). After 2 hours of stirring at ambient temperature, the mixture was washed with H$_2$O and the layers separated. The organic extract was dried and concentrated. Purification by column chromatography using an Analogix® Intelliflash280™ (SiO$_2$, 0-40% MeOH in dichloromethane) afforded the title compound as white solid (250 mg, 61.4% yield). $^1$H NMR (300 MHz, DMSO-d$_6$) δ ppm 0.94 (t, J=7.29 Hz, 3H) 1.33 (d, J=6.44 Hz, 3H) 1.36-1.47 (m, 2H) 1.77-1.87 (m, 2H) 2.02-2.04 (m, 1H) 2.09 (s, 6H) 2.17-2.28 (m, 2H) 3.00 (q, J=6.67 Hz, 2H) 4.20 (d, J=4.41 Hz, 2H) 4.54 (t, J=7.46 Hz, 2H) 4.97-5.07 (m, 1H) 7.02 (t, J=5.59 Hz, 1H) 7.37 (d, J=8.48 Hz, 1H) 7.84 (dd, J=8.81, 2.37 Hz, 1H) 8.01 (d, J=5.42 Hz, 1H) 8.28 (d, J=2.03 Hz, 1H) 8.50 (d, J=5.42 Hz, 1H) 9.04 (s, 1H); MS (DCI/NH$_3$) m/z 568 (M+H)$^+$.

The solid was diluted with EtOAc (10 mL) and sulfuric acid (1 mL) was added slowly at 0° C. The resulting white solid was collected by filtration to yield the bisulfate salt. $^1$H NMR (300 MHz, CD$_3$OD) δ ppm 1.05 (t, J=7.46 Hz, 3H) 1.44 (d, J=6.44 Hz, 3H) 1.48-1.61 (m, 2H) 1.89-2.01 (m, 2H) 2.92 (s, 6H) 3.20-3.29 (m, 2H) 3.42-3.56 (m, 2H) 4.21-4.35 (m, 2H) 4.56-4.69 (m, 2H) 5.18-5.28 (m, 1H) 7.36 (d, J=8.82 Hz, 1H) 7.84 (dd, J=8.82, 2.03 Hz, 1H) 8.44-8.54 (m, 2H) 8.65 (d, J=6.10 Hz, 1H) 9.22 (s, 1H); MS (DCI/NH$_3$) m/z 568 (M+H)$^+$. Anal. Calcd for C$_{26}$H$_{32}$F$_3$N$_5$O$_4$S.2H$_2$SO$_4$.2H$_2$O: C, 39.04; H, 5.04; N, 8.76. Found: 39.13; H, 4.93; N, 8.73.

Example 16

(3S)-4-({(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl}oxy)-3-amino-4-oxobutanoic acid

Example 16A (S)-4-tert-butyl 1-((S)-1-(2-((Z)-3-butylthiazolo[4,5-c]pyridin-2(3H)-ylidenecarbamoyl)-4-(trifluoromethyl)phenoxy)propan-2-yl) 2-(tert-butoxycarbonylamino)succinate To a solution of Example 18C (0.380 g, 0.838 mmol), triethylamine (0.584 ml, 4.19 mmol), (S)-4-tert-butoxy-2-(tert-butoxycarbonylamino)-4-oxobutanoic acid (0.242 g, 0.838 mmol), DMAP (0.026 g, 0.209 mmol) in DMF (10 mL) added HATU (0.794 g, 2.095 mmol). The mixture was stirred overnight at room temperature then diluted with ice water (50 mL). The solid was collected by filtration to give the title compound (490 mg, 0.676 mmol, 81% yield). $^1$H NMR (300 MHz, DMSO-d$_6$) δ ppm 0.95 (t, J=7.29 Hz, 3H) 1.23-1.28 (m, 7H) 1.29-1.36 (m, 13H) 1.36-1.46 (m, 4H) 1.76-1.89 (m, 2H) 2.36-2.47 (m, 1H) 2.60-2.73 (m, 1H) 4.18-4.33 (m, 3H) 4.54 (t, J=7.12 Hz, 2H) 5.13-5.23 (m, 1H) 7.37 (d, J=8.81 Hz, 1H) 7.85 (dd, J=8.81, 2.37 Hz, 1H) 7.99 (t, J=4.75 Hz, 1H) 8.31 (d, J=2.71 Hz, 1H) 8.50 (d, J=5.09 Hz, 1H) 9.04 (s, 1H); MS (DCI/NH$_3$) m/z 725 (M+H)$^+$.

Example 16B (3S)-4-({(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl}oxy)-3-amino-4-oxobutanoic acid To a solution of Example 16A (380 mg, 0.524 mmol) in EtOAc was added a solution of hydrogen chloride in dioxane (3.93 ml, 15.73 mmol). The mixture was stirred overnight at room temperature resulting in formation of a precipitate. The mixture was concentrated and the solids were dissolved in MeOH and EtOAc was added. The solid was filtered to obtain the title compound as the HCl salt. $^1$H NMR (300 MHz, CD$_3$OD) δ ppm 1.03-1.09 (m, 3H) 1.46-1.60 (m, 5H) 1.86-1.99 (m, 2H) 3.01-3.14 (m, 2H) 4.26-4.32 (m, 1H) 4.35-4.48 (m, 2H) 4.64 (t, J=7.54 Hz, 2H) 5.43-5.54 (m, 1H) 7.32-7.39 (m, 1H) 7.85 (d, J=8.72 Hz, 1H) 8.49-8.57 (m, 2H) 8.67 (d, J=5.95 Hz, 1H) 9.27 (s, 1H); MS (APCI/NH$_3$) m/z 569 (M+H)$^+$.

Example 17

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-(dimethylamino)ethyl carbonate The title compound was prepared as described in Example 15, substituting 2-(dimethylamino)ethanol for N,N-dimethylethylene diamine. $^1$H NMR (300 MHz, DMSO-D$_6$) δ ppm 0.94 (t, J=7.46 Hz, 3H) 1.37 (d, J=6.44 Hz, 3H) 1.39-1.46 (m, 2H) 1.77-1.87 (m, 2H) 2.07 (s, 6H) 2.40 (t, J=5.76 Hz, 2H) 4.07 (t, J=5.43 Hz, 2H) 4.19-4.26 (m, 1H) 4.29-4.36 (m, 1H) 4.49-4.59 (m, 2H) 5.05 (td, J=6.27, 3.73 Hz, 1H) 7.37 (d, J=8.82 Hz, 1H) 7.85 (dd, J=8.82, 2.03 Hz, 1H) 8.01 (d, J=6.10 Hz, 1H) 8.27 (d, J=2.37 Hz, 1H) 8.50 (d, J=5.09 Hz, 1H) 9.04 (s, 1H); MS (DCI/NH$_3$) m/z 568 (M+H)$^+$. The sulfate salt was obtained in analogous manner. $^1$H NMR (300 MHz, CD$_3$OD) δ ppm 1.05 (t, J=7.34 Hz, 3H) 1.47 (d, J=6.74 Hz, 3H) 1.51-1.60 (m, 2H) 1.90-2.01 (m, 2H) 2.93 (s, 6H) 3.51-3.55 (m, 2H) 4.23-4.36 (m, 2H) 4.53 (q, J=4.63 Hz, 2H) 4.59-4.66 (m, 2H) 5.28 (td, J=6.54, 3.57 Hz, 1H) 7.34 (d, J=8.72 Hz, 1H) 7.84 (dd, J=8.92, 2.18 Hz, 1H) 8.47 (d, J=1.98 Hz, 1H) 8.57 (d, J=6.35 Hz, 1H) 8.67 (d, J=5.95 Hz, 1H) 9.25 (s, 1H); MS (DCI/NH$_3$) m/z 569 (M+H)$^+$. Anal. Calcd for C$_{26}$H$_{32}$F$_3$N$_4$O$_5$S.2.2H$_2$SO$_4$.2.0H$_2$O: C, 37.20; H, 5.09; N, 6.67. Found: C, 37.20; H, 4.72; N, 6.61.

Example 18

N-[(2Z)-3-butyl[1,3]thiazolo[4,5-c]pyridin-2(3H)-ylidene]-2-{[(2S)-2-hydroxypropyl]oxy}-5-(trifluoromethyl)benzamide

Example 18A 2-fluoro-N-(thiazolo[4,5-c]pyridin-2-yl)-5-(trifluoromethyl)benzamide A mixture of thiazolo[4,5-c]pyridin-2-amine (Milestone Pharm Tech USA Inc.) (1.35 g, 8.93 mmol), 2-fluoro-5-(trifluoromethyl)benzoic acid (2.23 g, 10.72 mmol) and triethylamine (2.71 g, 26.8 mmol) in THF (30 mL) was treated drop wise with 1-propanephosphonic acid cyclic anhydride (50% in ethyl acetate) (6.82 g, 10.72 mmol). The mixture was stirred at room temperature for 12 hrs. The reaction mixture was diluted with EtOAc, and washed with saturated NaHCO$_3$. The organic layer was dried (Na$_2$SO$_4$), filtered, and concentrated. The residue was triturated with Et$_2$O and hexane to afford the title compound (2.2 g, 72%) as a brown solid. $^1$H NMR (500 MHz, DMSO-d$_6$) δ ppm 7.66 (t, J=9.46 Hz, 1H) 8.07 (m, 1H) 8.12 (d, J=4.88 Hz, 1H) 8.26 (dd, J=6.10, 2.14 Hz, 1H) 8.44 (d, J=5.49 Hz, 1H) 9.07 (s, 1H); MS (DCI/NH$_3$) m/z 342 (M+1)$^+$.

Example 18B

N-[(2Z)-3-butyl[1,3]thiazolo[4,5-c]pyridin-2(3H)-ylidene]-2-fluoro-5-(trifluoromethyl)benzamide A mixture of the product from Example 18A (240 mg, 0.70 mmol), potassium carbonate (195 mg, 1.41 mmol), tetrabutylammonium hydrogensulfate (7.2 mg, 0.02 mmol), tetrabutylammonium iodide (7.8 mg, 0.02 mmol), tetraethylammonium iodide (5.4 mg, 0.02 mmol) and 1-iodobutane (241 μL, 2.11 mmol) in toluene (30 mL) was refluxed for 12 hrs. The reaction mixture was cooled to ambient temperature, diluted with EtOAc, and washed with saturated NaHCO$_3$. The organic layer was dried (Na$_2$SO$_4$), filtered, and concentrated. The residue was purified by column chromatography using an Analogix® Intelliflash280™ (SiO$_2$, 0-50% ethyl acetate in hexanes) to afford the title compound (89 mg, 32%). MS (ESI$^+$) m/z 398 (M+H)$^+$.

Example 18C

N-[(2Z)-3-butyl[1,3]thiazolo[4,5-c]pyridin-2(3H)-ylidene]-2-{[(2S)-2-hydroxypropyl]oxy}-5-(trifluoromethyl)benzamide (S)-propane-1,2-diol (52 mg, 0.68 mmol) in THF (1 mL) was treated with NaH (60% dispersion; 27 mg, 0.68 mmol) at room temperature for 20 minutes. The mixture was cooled to 0° C. and a solution of Example 18B (90 mg, 0.23 mmol) in THF (1 mL) was added. The mixture was allowed to warm to room temperature, and stirred for 4 hours. The mixture was diluted with saturated aqueous NaHCO$_3$ (20 mL) and extracted with ethyl acetate (2×30 mL). The combined organic extracts were dried over anhydrous Na$_2$SO$_4$, filtered, and concentrated. The residue was purified by column chromatography using an Analogix® Intelliflash280™ (SiO$_2$, 0-100% ethyl acetate in hexanes) to afford 19 mg (19%) of the title compound. $^1$H NMR (500 MHz, CDCl$_3$) δ ppm 1.04 (t, J=7.48 Hz, 3H) 1.28 (d, J=6.41 Hz, 3H) 1.47-1.59 (m, 2H) 1.88-1.98 (m, 2H) 3.87 (t, J=8.85 Hz, 1H) 4.21-4.31 (m, 1H) 4.35 (dd, J=9.15, 2.75 Hz, 1H) 4.51-4.59 (m, 2H) 7.12 (d, J=8.85 Hz, 1H) 7.72 (dd, J=8.54, 2.14 Hz, 2H) 8.51 (d, J=1.83 Hz, 2H) 8.75 (s, 1H); MS (DCI/NH$_3$) m/z 454 (M+H)$^+$.

Example 19

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl L-prolinate Example 18C and (S)-1-(tert-butoxycarbonyl)pyrrolidine-2-carboxylic acid (Aldrich) were processed as described in Examples 2A and 2B to afford the title compound. $^1$H NMR (DMSO-d$_6$) δ 0.94 (t, J=7.3 Hz, 3H), 1.31 (d, J=6.7 Hz, 3H), 1.37-1.48 (m, 4H), 1.56-1.67 (m, 1H), 1.74-1.86 (m, 3H), 2.59-2.67 (m, 1H), 2.73-2.81 (m, 1H), 3.53-3.57 (m, 1H), 4.17-4.23 (m, 1H), 4.28-4.33 (m, 1H), 4.48-4.58 (m, 2H), 5.14-5.24 (m, 1H), 7.38 (d, J=8.7 Hz, 1H), 7.85 (dd, J=8.9, 2.2 Hz, 1H), 8.03 (d, J=5.2 Hz, 1H), 8.23 (d, J=2.0 Hz, 1H), 8.50 (d, J=5.2 Hz, 1H), 9.04 (s, 1H). MS (ESI+) m/z 551 (M)$^+$.

The hydrogen chloride salt of the title compound was prepared as described in Example 2B. MS (ESI$^+$) m/z 551 (M+H)$^+$.

Example 20

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl D-alaninate Example 18C and (R)-2-(tert-butoxycarbonylamino)propanoic acid (Alfa) were processed as described in Examples 2A and 2B to afford the title compound. $^1$H NMR (DMSO-d$_6$) δ 0.94 (t, J=7.8 Hz, 3H), 1.11 (d, J=6.8 Hz, 3H), 1.32 (d, J=6.4 Hz, 3H), 1.35-1.47 (m, 2H), 1.70 (br s, 2H), 1.77-1.87 (m, 2H), 3.30-3.37 (m, 1H), 4.19-4.31 (m, 2H), 4.51-4.56 (m, 2H), 5.13-5.22 (m, 1H), 7.38 (d, J=8.8 Hz, 1H), 7.85 (dd, J=9.0, 2.2 Hz, 1H), 8.02 (dd, J=5.1, 0.7 Hz, 1H), 8.27 (d, J=2.4 (Hz, 1H), 8.50 (d, J=5.1 Hz, 1H), 9.04 (s, 1H). MS (ESI$^+$) m/z 525 (M)$^+$.

The hydrogen chloride salt of the title compound was prepared as described in Example 2B. MS (ESI$^+$) m/z 525 (M+H)$^+$.

Example 21

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl[1-(aminomethyl)cyclohexyl]acetate Example 18C and 2-(1-(tent-butoxycarbonylamino)cyclohexyl)acetic acid (Astatech) were processed as described in Examples 2A and 2B, except that an etheric solution of hydrogen chloride was utilized instead of trifluoroacetic acid to deprotect the tert-butoxycarbonyl intermediate, and that the reaction mixture was concentrated to provide the hydrogen chloride salt of the title compound. MS of HCl salt (ESI$^+$) m/z 607 (M+H)$^+$.

Example 22

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl acetate Example 18C (502 mg, 1.12 mmol) in THF (20 mL) was treated with sodium tert-butoxide (106 mg, 1.12 mmol) at 0 to 5° C. for 30 minutes. Then, 2-(chlorocarbonyl)phenyl acetate (220 mg, 1.12 mmol) was added and the mixture was stirred at room temperature for 12 hours. After removing the volatiles under reduced pressure, the residue was treated with a 5% aqueous solution of acetic acid (to pH ~5) and extracted with EtOAc. The organic extract was washed with saturated aqueous NaHCO$_3$ and brine, dried with anhydrous MgSO$_4$, filtered, and concentrated under reduced pressure. The residue was purified by chromatography (hexane-EtOAc 1:2) to afford 200 mg of the title compound. $^1$H NMR (300 MHz, DMSO-d$_6$) δ ppm 0.94 (t, J=7.29 Hz, 3H) 1.32 (d, J=6.44 Hz, 3H) 1.35-1.47 (m, 2H) 1.77-1.86 (m, 2H) 1.98 (s, 3H) 4.12-4.33 (m, 2H) 4.54 (t, J=7.46 Hz, 2H) 5.12-5.24 (m, 1H) 7.37 (d, J=8.81 Hz, 1H) 7.85 (dd, J=8.98, 2.20 Hz, 1H) 8.03 (d, J=5.09 Hz, 1H) 8.27 (d, J=2.03 Hz, 1H) 8.50 (d, J=5.09 Hz, 1H) 9.04 (s, 1H); MS m/z 496 (M+H)$^+$.

Example 23

(2R)-1-[2-{[(2Z)-3-butyl[1,3]thiazolo[4,5-c]pyridin-2(3H)-ylidene]carbamoyl}-4-(trifluoromethyl)phenoxy]propan-2-yl D-alaninate

Example 23A

N-[(2Z)-3-butyl[1,3]thiazolo[4,5-c]pyridin-2(3H)-ylidene]-2-{[(2S)-2-hydroxypropyl]oxy}-5-(trifluoromethyl)benzamide Example 18B and (R)-propane-1,2-diol were processed as described in Example 18A to afford the title compound. MS-ESI: 454 (M+1); $^1$H-NMR (DMSO-$d_6$) δ 0.93 (3H, t, J=7.5 Hz), 1.19 (3H, d, J=5.8 Hz), 1.40 (2H, m), 1.81 (2H, m), 4.00 (3H, m), 4.52 (2H, t, J=7.5 Hz), 4.88 (1H, s), 7.34 (1H, d, J=8.6 Hz), 7.81 (1H, dd, J=8.6, 2.2 Hz), 7.99 (1H, d, J=5.2 Hz), 8.24 (1H, d, J=2.2 Hz), 8.48 (1H, d, J=5.2 Hz), 9.01 (1H, s).

Example 23B (2R)-1-[2-{[(2Z)-3-butyl[1,3]thiazolo[4,5-c]pyridin-2(3H)-ylidene]carbamoyl}-4-(trifluoromethyl)phenoxy]propan-2-yl D-alaninate Example 23A and N-α-(tert-butoxycarbonyl)-D-alanine (Aldrich)) were processed as described in Examples 2A and 2B to afford the title compound. $^1$HNMR in DMSO-$d_6$: 0.93 (3H, t, J=7.4 Hz), 1.03 (3H, d, J=6.8 Hz), 1.31 (3H, d, J=6.4 Hz), 1.39 (2H, m), 1.68 (2H, s, br, NH$_2$), 1.80 (2H, m), 3.30 (1H, q, J=7.0 Hz), 4.18 (1H, dd, J=10.6, 6.7 Hz), 4.28 (1H, dd, J=10.6, 3.9 Hz), 4.52 (2H, m), 5.15 (1H, m), 7.36 (1H, d, J=8.8 Hz), 7.82 (1H, dd, J=8.8, 2.4 Hz), 8.00 (1H, d, J=5.1 Hz), 8.22 (1H, d, J=2.4 Hz), 8.47 (1H, d, J=5.1 hz), 9.02 (1H, s). MS (ESI$^+$) m/z 525 (M+H)$^+$, 1049 (2M+H)$^+$.

j. IN VIVO DATA

Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Spinal Nerve Ligation Model of Neuropathic Pain

A spinal nerve ligation-induced (SNL) model of neuropathic pain as originally described by Kim and Chung (Kim, S. H. and J. M. Chung, 1992, Pain 50, 355) was used to test the compounds of the present application. The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds was also assessed in several control groups, including naive, sham-operated, and saline infused animals as well as in the contralateral paws of nerve-injured rats. Compounds tested showed a statistically significant change in paw withdrawal latency versus vehicle at less than about 300 micromoles/kg, for example, at less than about 100 micromoles/kg.

Sodium Iodoacetate-Induced Knee Joint Osteoarthritic Pain Model

Unilateral knee joint osteoarthritis was induced in the rats by a single intraarticular (i.a.) injection of sodium iodoacetate (3 mg in 0.05 mL sterile isotonic saline) into the right knee joint cavity under light isoflurane anesthesia using a 26G needle. The dose of the sodium iodoacetate (3 mg/i.a. injection) was selected based on results obtained from preliminary studies wherein an optimal pain behavior was observed at this dose. Pain behavioral assessment of hind limb grip force was conducted by recording the maximum compressive force exerted on the hind limb strain gauge setup, in a commercially available grip force measurement system (Columbus Instruments, Columbus, Ohio). The grip force data was converted to a maximum hind limb cumulative compressive force (CF-max) (gram force)/kg body weight for each animal. The analgesic effects of test compounds were determined 20 days following the i.a. injection of sodium iodoacetate. The vehicle control group for each compound being tested was assigned 0% whereas the age matched naïve group was assigned as being 100% (normal). The % effect for each dose group was then expressed as % return to normalcy compared to the naïve group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing can last for any time greater than one day. A typical duration of repeated daily dosing is about 5 days to about 12 days.

Compounds tested showed a statistically significant change in hind limb grip force strength versus vehicle at less than about 300 micromoles/kg in the iodoacetate-induced model of osteoarthritic pain following a single dose, for example, at less than about 50 micromoles/kg in the iodoacetate-induced model of osteoarthritic pain following a single dose. Compounds tested also showed a statistically significant change in hind limb grip force strength versus vehicle at less than about 30 μmoles/kg in the iodoacetate-induced model of osteoarthritic pain following repeated daily administration for 5 to 12 days, for example, at less than about 5 micromoles/kg in the iodoacetate-induced model of osteoarthritic pain following repeated daily administration for 5 to 12 days.

Chronic Constriction Injury Model of Neuropathic Pain

A chronic constriction injury-induced (CCI) model of neuropathic pain was produced in rats by following the method of Bennett and Xie (Pain, 1988, 33:87). Following sterilization and anesthetic procedures, a 1.5 cm incision was made dorsal to the pelvis, and the biceps femoris and gluteous superficialis (right side) were separated. The right common sciatic nerve was exposed/isolated, and loosely ligated by 4 ligatures of chromic gut (5-0) with <1 mm spacing using hemostats and forceps. The wound was sutured (layer of muscle closed with 6.0 absorbable sutures, and the skin closed with wound clips or tissue glue. The animals were allowed to recover on a warming plate and were returned to their home cages (soft bedding) when able to walk on their own. Loose ligation of the sciatic nerve in rats would lead to the development of neuropathic pain within two weeks. Compounds were tested in the animals two or three weeks post-surgery.

In tactile stimulation experiments, tactile allodynia was measured using calibrated von Frey filaments (Stoelting, Wood Dale, Ill.) as previously described. Rats were placed into inverted individual plastic containers (20×12.5×20 cm) on top of a suspended wire mesh grid, and acclimated to the test chambers for 20 min. The von Frey filaments with different bending forces (starting with the lowest first and then progressively increasing) were presented perpendicularly to the plantar surface of the selected hind paw, and then hold in this position for approximately 8 sec with enough force to cause a slight bend in the filament. Positive responses included an abrupt withdrawal of the hind paw from the stimulus, or flinching behavior immediately following removal of the stimulus. Compounds tested in the CCI model of neuropathic pain showed a statistically significant change in paw withdrawal latency versus vehicle at less than about 300 micromoles/kg, for example, at less than about 100 micromoles/kg. A compound tested also showed a statistically significant change in tactile allodynia versus a saline vehicle at less than about 100 micromoles/kg in the CCI model of neuropathic pain following repeated daily administration for 5 to 12 days, for example, at less than about 30 micromoles/kg in the CCI model of neuropathic pain following repeated daily administration for 5 to 12 days.

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

The invention claimed is:

1. A compound of formula (III)

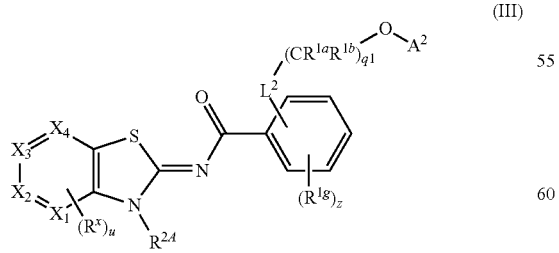

or a pharmaceutically acceptable salt, solvate, or salt of solvate thereof, wherein $L^2$ is O, or $N(R^{bx})$; wherein $R^{bx}$ is hydrogen, alkyl, or haloalkyl;

$A^2$ is hydrogen, $—S(O)_2(OH)$, $—P(=O)(OH)(OH)$, $—(CR^{1e}R^{1f})_{q2}OP(=O)(OH)(OH)$, $—(CR^{1e}R^{1f})_{q2}OS(O)_2(OH)$, $—C(O)R^z$, $—C(O)(CR^{1c}R^{1d})_{q2}N(R^{aa})(R^{ab})$, $—C(O)O(CR^{1c}R^{1d})_{q4}N(R^{aa})(R^{ab})$, $—C(O)(CR^{1e}R^{1f})_{q2}C(O)OH$, $—C(O)(CR^{1e}R^{1f})_{q2}OP(=O)(OH)(OH)$, $—C(O)N(R^{aa})(—(CR^{1e}R^f)_{q4}—N(R^{ac})R^{ad}))$, or $—C(O)(CR^{1e}R^{1f})_{q2}C(O)N(R^{ad})(R^{ab})$;

$R^z$ is alkyl, $G^{1a}$, or $—(CR^{1c}R^{1d})_{q2}G^{1a}$; wherein $G^{1a}$ is phenyl, monocyclic heteroaryl, monocyclic cycloalkyl, monocyclic cycloalkenyl, or monocyclic heterocycle $R^{ab}$, at each occurrence, is independently hydrogen, $C_1$-$C_6$ alkyl, haloalkyl, or $—(CR^{1e}R^{1f})_{q4}—N(R^{ac})(R^{ad})$;

each occurrence of $R^{1a}$, $R^{1b}$, $R^{1c}$, $R^{1e}$, $R^{1f}$, $R^{aa}$, $R^{ac}$, and $R^{ad}$, are each independently hydrogen, $C_1$-$C_6$ alkyl, or haloalkyl;

each occurrence of $R^{1d}$ is independently hydrogen, $C_1$-$C_6$ alkyl, haloalkyl, alkoxyalkyl, hydroxyalkyl, $—(CR^{1e}R^{1f})_{q3}—N(R^{ac})(R^{ad})$, or $—(CR^{1e}R^{1f})_{q3}—COOH$;

q1, q2, and q3, at each occurrence, are each independently 1, 2, 3, or 4;

$R^{2A}$ is $C_2$-$C_{10}$ alkyl, haloalkyl, or $—(CR^{2a}R^{2b})_{q6}$-$G^{2a}$;

$R^a$, $R^b$, and $R^c$, at each occurrence, are each independently hydrogen, alkyl, or haloalkyl;

$R^d$ is alkyl or haloalkyl;

$R^{2a}$, and $R^{2b}$, at each occurrence, are each independently hydrogen, halogen, $C_1$-$C_4$ haloalkyl, or $C_1$-$C_6$ alkyl;

q4, at each occurrence, is independently 2, 3, 4, or 5;

q6, at each occurrence, are each independently 1, 2, 3, or 4;

$R^x$ is an optional substituent on one or more substitutable carbon atom, and each $R^x$ is independently selected from the group consisting of alkyl, halogen, hydroxy, alkoxy, haloalkoxy, and haloalkyl;

u is 0, 1, 2, or 3;

one or two of $X_1$, $X_2$, $X_3$, and $X_4$ is N or $N^+$-Q, and the others are CH; with the proviso that when $A^2$ is hydrogen, then at least one of $X_1$, $X_2$, $X_3$, and $X_4$ is $N^+$-Q;

Q is $O^-$, $—(CR^{qe}R^{qf})—OP(=O)OH)(OH)$, $—(CR^{qe}R^{qf})—OS(O)_2(OH)$, $—(CR^{qe}R^{qf})—OC(O)R^p$, or formula (i)

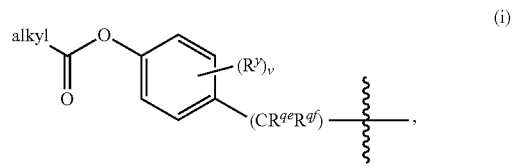

$R^p$ is alkyl, $N(R^q)(R^u)$, phenyl, monocyclic heterocycle, $—(CR^{qe}R^{qd})_{q7}—N(R^q)(R^u)$, $—N(R^q)(—(CR^{qe}R^{qf})_{q4}—N(R^q)(R^u))$, $—N(R^q)(—(CR^{qe}R^{qf})_{q4}—O(R^u))$, $—(CR^{qe}R^{qf})_{q7}—C(O)OH$, $—(CR^{qe}R^{qf})_{q7}—OP(=O)(OH)(OH)$, or $—(CR^{qe}R^{qd})_{q7}—C(O)N(R^q)(—(CR^{qe}R^{qf})_{q7}—N(R^q)(R^u))$, wherein the phenyl and the monocyclic heterocycle moieties are each independently unsubstituted or substituted with one or two substituents independently selected from the group consisting of alkyl, haloalkyl, OH, alkoxy, C(O)OH, C(O)O(alkyl), and halogen;

$R^y$ is alkyl;

v is 0, 1, 2, or 3;

each occurrence of $R^{3a}$, $R^{3b}$, $R^{qc}$, $R^{qe}$, $R^{qf}$, $R^q$, and $R^u$, are each independently hydrogen, $C_1$-$C_6$ alkyl, or haloalkyl;

each occurrence of $R^{qd}$ is independently hydrogen, $C_1$-$C_6$ alkyl, haloalkyl, alkoxyalkyl, hydroxyalkyl, —$(CR^{qe}R^{qf})_{q8}$—$N(R^q)(R^u)$, or —$(CR^{qe}R^{qf})_{q8}$—COOH;

q7 and q8, at each occurrence, are each independently 1, 2, or 3;

$G^{2a}$ is cycloalkyl;

each ring as represented by $G^{1a}$, and $G^{2a}$ is independently unsubstituted or substituted 1, 2, 3, 4, or 5 substituents independently selected from the group consisting of oxo, alkyl, halogen, hydroxy, alkoxy, $NH_2$, N(H)(alkyl), N(alkyl)$_2$, haloalkoxy, haloalkyl, —($C_1$-$C_6$ alkylenyl)-$NH_2$, —($C_1$-$C_6$ alkylenyl)-NH(alkyl), and —($C_1$-$C_6$ alkylenyl)-N(alkyl)$_2$;

$R^{1g}$, at each occurrence, is independently $C_1$-$C_4$ alkyl, $C_2$-$C_4$ alkenyl, $C_2$-$C_4$ alkynyl, halogen, $C_1$-$C_4$ haloalkyl, —CN, or —$OR^f$;

$R^f$, at each occurrence, is independently hydrogen, $C_1$-$C_6$ alkyl, or $C_1$-$C_4$ haloalkyl; and z is 0, 1, 2, 3, or 4.

2. The compound of formula (III) according to claim 1 or a pharmaceutically acceptable salt, solvate, or salt of solvate thereof, wherein

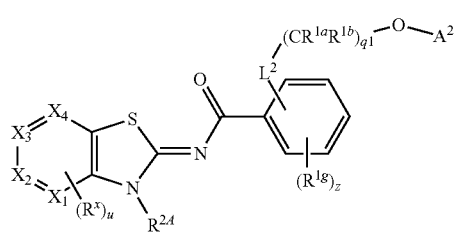

one of $X_1$, $X_2$, $X_3$, and $X_4$ is N and the others are CH; and $A^2$ is —P(=O)(OH)(OH), —C(O)$R^z$, —C(O)$(CR^{1c}R^{1d})_{q2}N(R^{aa})(R^{ab})$, —C(O)O$(CR^{1c}R^{1d})_{q4}N(R^{aa})(R^{ab})$, —C(O)$(CR^{1e}R^{1f})_{q2}$C(O)OH, or —C(O)N($R^{aa}$)(—$(CR^{1e}R^{1f})_{q4}$—N($R^{ac}$)($R^{ad}$)).

3. The compound of formula (III) according to claim 2 or a pharmaceutically acceptable salt, solvate, or salt of solvate thereof, wherein $X_2$ is N; and $X_1$, $X_3$, and $X_4$ are CH.

4. The compound of formula (III) according to claim 3 or a pharmaceutically acceptable salt, solvate, or salt of solvate thereof, wherein $R^{2A}$ is $C_2$-$C_{10}$ alkyl or haloalkyl.

5. The compound of formula (III) according to claim 4 or a pharmaceutically acceptable salt, solvate, or salt of solvate thereof, wherein $R^{2A}$ is $C_2$-$C_{10}$ alkyl.

6. The compound of formula (III) according to claim 5 or a pharmaceutically acceptable salt, solvate, or salt of solvate thereof, wherein $L^2$ is O.

7. The compound of formula (III) according to claim 6 or a pharmaceutically acceptable salt, solvate, or salt of solvate thereof, wherein $R^{1a}$ and $R^{1b}$ are the same or different, and are each independently hydrogen or $C_1$-$C_6$ alkyl, and q1 is 2.

8. The compound of formula (III) according to claim 2 or a pharmaceutically acceptable salt, solvate, or salt of solvate thereof, wherein $X_4$ is N; and $X_1$, $X_2$, and $X_3$ are CH.

9. The compound of formula (III) according to claim 1 or a pharmaceutically acceptable salt, solvate, or salt of solvate thereof, wherein

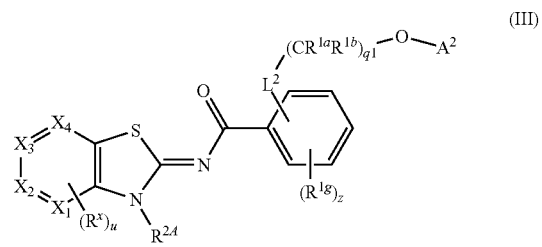

one of $X_1$, $X_2$, $X_3$, and $X_4$ is $N^+$-Q and the others are CH; and $A^2$ is hydrogen.

10. The compound of formula (III) according to claim 9 or a pharmaceutically acceptable salt, solvate, or salt of solvate thereof, wherein $X_2$ is $N^+$-Q; and $X_1$, $X_3$, and $X_4$ are CH.

11. The compound of formula (III) according to claim 10 or a pharmaceutically acceptable salt, solvate, or salt of solvate thereof, wherein Q is $O^-$, —$(CR^{qe}R^{qf})$—OC(O)$R^p$, or formula (i).

12. The compound of formula (III) according to claim 11 or a pharmaceutically acceptable salt, solvate, or salt of solvate thereof, wherein $R^{2A}$ is $C_2$-$C_{10}$ alkyl or haloalkyl.

13. The compound of formula (III) according to claim 12 or a pharmaceutically acceptable salt, solvate, or salt of solvate thereof, wherein $R^{2A}$ is $C_2$-$C_{10}$ alkyl.

14. The compound of formula (III) according to claim 13 or a pharmaceutically acceptable salt, solvate, or salt of solvate thereof, wherein $L^2$ is O.

15. The compound of formula (III) according to claim 14 or a pharmaceutically acceptable salt, solvate, or salt of solvate thereof, wherein $R^{1a}$ and $R^{1b}$ are the same or different, and are each independently hydrogen or $C_1$-$C_6$ alkyl, and q1 is 2.

16. The compound according to claim 1 or a pharmaceutically acceptable salt, solvate, or salt of solvate thereof, wherein $R^{2A}$ is $C_2$-$C_{10}$ alkyl or haloalkyl.

17. The compound according to claim 1 or a pharmaceutically acceptable salt, solvate, or salt of solvate thereof, wherein $R^{2A}$ is $C_2$-$C_{10}$ alkyl.

18. The compound according to claim 1 or a pharmaceutically acceptable salt, solvate, or salt of solvate thereof, wherein $L^2$ is O.

19. The compound according to claim 18 or a pharmaceutically acceptable salt, solvate, or salt of solvate thereof, wherein $R^{2A}$ is $C_2$-$C_{10}$ alkyl.

20. The compound of claim 1 selected from the group consisting of (2Z)-5-[(acetyloxy)methyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium;

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-methylalaninate;

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl glycinate;

(2Z)-3-butyl-5-{[(2,2-dimethylpropanoyl)oxy]methyl}-2-{[2-{[(2S)-2-hydroxypropyl]oxy}-5-(trifluoromethyl)benzoyl]imino}-2,3-dihydro[1,3]thiazolo[4,5-c]pyridin-5-ium;

(2Z)-5-[(benzoyloxy)methyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium;

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl L-alaninate;

(2Z)-3-butyl-2-{[2-{[(2S)-2-hydroxypropyl]oxy}-5-(trifluoromethyl)benzoyl]imino}-5-[({[(2S)-2-(methoxycarbonyl)pyrrolidin-1-yl]carbonyl}oxy)methyl]-2,3-dihydro[1,3]thiazolo[4,5-c]pyridin-5-ium;

(2Z)-3-butyl-5-({[(dimethylamino)carbonyl]oxy}methyl)-2-{[2-{[(2S)-2-hydroxypropyl]oxy}-5-(trifluoromethyl)benzoyl]imino}-2,3-dihydro[1,3]thiazolo[4,5-c]pyridin-5-ium;

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl dihydrogen phosphate;

(2Z)-3-butyl-2-{[2-{[(2S)-2-hydroxypropyl]oxy}-5-(trifluoromethyl)benzoyl]imino}-5-[({[(3-methoxypropyl)amino]carbonyl}oxy)methyl]-2,3-dihydro[1,3]thiazolo[4,5-c]pyridin-5-ium;

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl N-methylglycinate;

N-[(2Z)-3-butyl-5-oxido[1,3]thiazolo[4,5-c]pyridin-2(3H)-ylidene]-2-{[(2S)-2-hydroxypropyl]oxy}-5-(trifluoromethyl)benzamide;

(2Z)-5-[4-(acetyloxy)-3,5-dimethylbenzyl]-3-butyl-2-{[2-{[(2S)-2-hydroxypropyl]oxy}-5-(trifluoromethyl)benzoyl]imino}-2,3-dihydro[1,3]thiazolo[4,5-c]pyridin-5-ium;

4-({(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl}oxy)-4-oxobutanoic acid;

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-(dimethylamino)ethylcarbamate;

(3S)-4-({(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl}oxy)-3-amino-4-oxobutanoic acid;

(1S)-2-[2-({[(2Z)-3-butyl[1,3]thiazolo[4,5-c]pyridin-2(3H)-ylidene]amino}carbonyl)-4-(trifluoromethyl)phenoxy]-1-methylethyl 2-(dimethylamino)ethyl carbonate;

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl L-prolinate;

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl D-alaninate;

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl[1-(aminomethyl)cyclohexyl]acetate;

(2S)-1-[2-{[(2Z)-3-butyl[1,3]thiazolo[4,5-c]pyridin-2(3H)-ylidene]carbamoyl}-4-(trifluoromethyl)phenoxy]propan-2-yl acetate; and (2R)-1-[2-{[(2Z)-3-butyl[1,3]thiazolo[4,5-c]pyridin-2(3H)-ylidene]carbamoyl}-4-(trifluoromethyl)phenoxy]propan-2-yl D-alaninate;

or a pharmaceutically acceptable salt, solvate, or salt of a solvate thereof.

21. A pharmaceutical composition comprising a therapeutically effective amount of a compound of formula (I) according to claim 1, or a pharmaceutically acceptable salt, solvate, or salt of a solvate thereof, and one or more pharmaceutically acceptable carriers.

22. A method for treating pain comprising administering to a mammal in need of such treatment a therapeutically effective amount of a compound of formula (I) according to claim 1, or a pharmaceutically acceptable salt, solvate, or salt of a solvate thereof, alone or in combination with one or more pharmaceutically acceptable carrier.

\* \* \* \* \*